United States Patent
Modlin et al.

(10) Patent No.: US 6,483,582 B2
(45) Date of Patent: Nov. 19, 2002

(54) APPARATUS AND METHODS FOR TIME-RESOLVED SPECTROSCOPIC MEASUREMENTS

(75) Inventors: Douglas N. Modlin, Palo Alto, CA (US); Todd E. French, Cupertino, CA (US); John C. Owicki, Palo Alto, CA (US)

(73) Assignee: LJL BioSystems, Inc., Sunnyvale, CA (US)

(*) Notice: Subject to any disclaimer, the term of this patent is extended or adjusted under 35 U.S.C. 154(b) by 0 days.

(21) Appl. No.: 09/765,874

(22) Filed: Jan. 19, 2001

(65) Prior Publication Data

US 2001/0003044 A1 Jun. 7, 2001

Related U.S. Application Data

(63) Continuation of application No. PCT/US99/16287, filed on Jul. 26, 1999.
(60) Provisional application No. 60/094,276, filed on Jul. 27, 1998.

(51) Int. Cl.[7] .................................................. G01J 3/30
(52) U.S. Cl. ........................ 356/317; 356/318; 356/323; 250/458.1; 250/459.1
(58) Field of Search .................................. 356/317, 323, 356/418, 246, 303, 318; 250/458.1, 459.1; 600/473, 317; 435/6

(56) References Cited

U.S. PATENT DOCUMENTS

| | | |
|---|---|---|
| 2,719,214 A | 9/1955 | Potter |
| 3,013,467 A | 12/1961 | Minsky |
| 3,423,581 A | 1/1969 | Baer |
| 3,516,736 A | 6/1970 | Weaver |
| 3,849,654 A | 11/1974 | Malvin |
| 3,885,162 A | 5/1975 | Geertz |

(List continued on next page.)

FOREIGN PATENT DOCUMENTS

| | | |
|---|---|---|
| EP | 0 222 341 A1 | 5/1987 |
| EP | 2 266 881 A2 | 11/1988 |
| EP | 0 977 037 A1 | 7/1999 |

(List continued on next page.)

OTHER PUBLICATIONS

*Standard Handbook for Electrical Engineers*, Donald G. Fink and H. Wayne Beaty, pp. 22–2 through 22–5, 11th ed., 1978.
*Fundamentals of Light Microscopy*, Spencer, Cambridge University Press, 1982.
Joseph R. Lakowicz, *Principles of Fluorescence Spectroscopy*, First Edition, Sep. 1983.

(List continued on next page.)

*Primary Examiner*—Frank G. Font
*Assistant Examiner*—Layla Lauchman
(74) *Attorney, Agent, or Firm*—Kolisch Hartwell PC

(57) ABSTRACT

Apparatus and methods for measuring light transmitted from a sample. The apparatus may include a stage, a light source, and a detector. The stage may be configured to hold a microplate having a plurality of sample wells. The apparatus may be configured to take frequency-domain time-resolved measurements of one or more of luminescence lifetimes and reorientational correlation times of a luminescent analyte in the sample.

106 Claims, 11 Drawing Sheets

U.S. PATENT DOCUMENTS

| | | |
|---|---|---|
| 3,932,023 A | 1/1976 | Humer |
| 4,011,451 A | 3/1977 | Nelson |
| 4,067,653 A | 1/1978 | Fletcher et al. |
| 4,074,939 A | 2/1978 | Rabl |
| 4,076,420 A | 2/1978 | De Maeyer et al. |
| 4,100,416 A | 7/1978 | Hirschfeld |
| 4,144,452 A | 3/1979 | Harte |
| 4,150,870 A | 4/1979 | d'Auria |
| 4,203,670 A | 5/1980 | Bromberg |
| 4,240,751 A | 12/1980 | Linnecke et al. |
| 4,296,326 A | 10/1981 | Halsop et al. |
| 4,397,560 A | 8/1983 | Andreson |
| 4,451,149 A | 5/1984 | Noeller |
| 4,451,433 A | 5/1984 | Yamashita et al. |
| 4,485,430 A | 11/1984 | Fustel |
| 4,501,970 A | 2/1985 | Nelson |
| 4,567,847 A | 2/1986 | Linner |
| 4,591,550 A | 5/1986 | Hafeman et al. |
| 4,626,684 A | 12/1986 | Landa |
| 4,646,214 A | 2/1987 | Mendleski |
| 4,661,770 A * | 4/1987 | von Roos ............... 324/158 D |
| 4,685,801 A | 8/1987 | Minekane |
| 4,699,512 A | 10/1987 | Koshi |
| 4,704,255 A | 11/1987 | Jolley |
| 4,707,067 A | 11/1987 | Haberland et al. |
| 4,730,921 A | 3/1988 | Klein et al. |
| 4,737,464 A | 4/1988 | McConnel et al. |
| 4,738,825 A | 4/1988 | Kelln et al. |
| 4,741,619 A | 5/1988 | Humphries et al. |
| 4,753,501 A | 6/1988 | Battle |
| 4,758,786 A | 7/1988 | Hafeman |
| 4,762,420 A | 8/1988 | Bowley |
| 4,772,453 A | 9/1988 | Lisenbee |
| 4,784,275 A | 11/1988 | Fridge |
| 4,802,768 A | 2/1989 | Gifford et al. |
| 4,808,828 A | 2/1989 | Kitamori et al. |
| 4,810,096 A | 3/1989 | Russel et al. |
| 4,826,660 A | 5/1989 | Smith et al. |
| 4,855,930 A | 8/1989 | Chao et al. |
| 4,868,103 A | 9/1989 | Stavrianopoulos et al. |
| 4,873,633 A | 10/1989 | Mezei et al. |
| 4,877,965 A | 10/1989 | Dandliker et al. |
| 4,885,087 A | 12/1989 | Kopf |
| 4,892,409 A | 1/1990 | Smith |
| 4,897,548 A | 1/1990 | Döme et al. |
| 4,923,819 A | 5/1990 | Fernandez et al. |
| 4,931,402 A | 6/1990 | Abplanalp |
| 4,936,682 A | 6/1990 | Hoyt |
| 4,948,442 A | 8/1990 | Manns |
| 4,963,815 A | 10/1990 | Hafeman |
| 4,968,148 A | 11/1990 | Chow et al. |
| 4,979,821 A | 12/1990 | Schutt et al. |
| 5,009,488 A | 4/1991 | Fay et al. |
| 5,018,866 A | 5/1991 | Osten |
| 5,020,995 A | 6/1991 | Levy |
| 5,034,613 A | 7/1991 | Denk et al. |
| 5,039,219 A | 8/1991 | James et al. |
| 5,047,215 A | 9/1991 | Manns |
| 5,058,045 A | 10/1991 | Ma |
| 5,082,628 A | 1/1992 | Andreotti et al. |
| 5,084,246 A | 1/1992 | Lyman et al. |
| 5,091,652 A | 2/1992 | Mathies et al. |
| 5,095,517 A | 3/1992 | Monguzzi et al. |
| 5,096,807 A | 3/1992 | Leaback |
| 5,164,319 A | 11/1992 | Hafeman et al. |
| 5,169,601 A | 12/1992 | Ohta et al. |
| 5,192,510 A | 3/1993 | Zoha et al. |
| 5,196,709 A | 3/1993 | Berndt et al. |
| 5,198,670 A | 3/1993 | VanCauter et al. |
| 5,206,568 A | 4/1993 | Björnson et al. |
| 5,208,161 A | 5/1993 | Saunders et al. |
| 5,208,651 A | 5/1993 | Buican |
| 5,216,488 A | 6/1993 | Tuunanen et al. |
| 5,225,164 A | 7/1993 | Astle |
| 5,257,202 A | 10/1993 | Feddersen et al. |
| 5,270,788 A | 12/1993 | Cercek et al. |
| 5,273,718 A | 12/1993 | Sköld et al. |
| 5,275,951 A | 1/1994 | Chow et al. |
| 5,281,825 A | 1/1994 | Berndt et al. |
| 5,289,407 A | 2/1994 | Strickler et al. |
| 5,307,144 A | 4/1994 | Hiroshi et al. |
| 5,315,015 A | 5/1994 | Hui et al. |
| 5,317,485 A | 5/1994 | Merjanian |
| 5,319,436 A | 6/1994 | Manns et al. |
| 5,323,008 A | 6/1994 | Studholme et al. |
| 5,323,010 A | 6/1994 | Gratton et al. |
| 5,340,716 A | 8/1994 | Ullman et al. |
| 5,340,747 A | 8/1994 | Eden |
| 5,341,215 A | 8/1994 | Seher |
| 5,353,112 A | 10/1994 | Smith |
| 5,355,215 A | 10/1994 | Schroeder et al. |
| 5,357,095 A | 10/1994 | Weyrauch et al. |
| 5,361,626 A | 11/1994 | Colligan et al. |
| 5,384,093 A | 1/1995 | Ootani et al. |
| 5,401,465 A | 3/1995 | Smethers et al. |
| 5,418,371 A | 5/1995 | Aslund et al. |
| 5,420,408 A | 5/1995 | Weyrauch et al. |
| 5,436,718 A | 7/1995 | Fernandes et al. |
| 5,445,935 A | 8/1995 | Royer |
| 5,449,921 A | 9/1995 | Baba |
| 5,457,527 A | 10/1995 | Manns et al. |
| 5,459,300 A | 10/1995 | Kasman |
| 5,480,804 A | 1/1996 | Niwa et al. |
| 5,485,530 A | 1/1996 | Lakowicz et al. |
| 5,487,872 A | 1/1996 | Hafeman et al. |
| 5,491,343 A | 2/1996 | Brooker |
| 5,500,188 A | 3/1996 | Hafeman et al. |
| 5,504,337 A | 4/1996 | Lakowicz et al. |
| 5,512,492 A | 4/1996 | Herron et al. |
| 5,523,573 A | 6/1996 | Hänninen et al. |
| 5,527,684 A | 6/1996 | Mabile et al. |
| 5,528,046 A | 6/1996 | Ishikawa |
| 5,537,343 A | 7/1996 | Kikinis et al. |
| 5,541,113 A | 7/1996 | Siddigi et al. |
| 5,542,012 A | 7/1996 | Fernandes et al. |
| 5,557,398 A | 9/1996 | Wechsler et al. |
| 5,561,068 A | 10/1996 | Rounbehler et al. |
| 5,589,136 A | 12/1996 | Northrup et al. |
| 5,589,350 A | 12/1996 | Bochner |
| 5,589,351 A | 12/1996 | Harootunian |
| 5,592,289 A | 1/1997 | Norris |
| 5,593,867 A | 1/1997 | Walker et al. |
| 5,595,710 A | 1/1997 | Van Dusen et al. |
| 5,599,500 A | 2/1997 | Jones |
| 5,604,130 A | 2/1997 | Warner et al. |
| 5,620,894 A | 4/1997 | Barger et al. |
| 5,626,134 A | 5/1997 | Zuckerman |
| 5,631,734 A | 5/1997 | Stern et al. |
| 5,633,724 A | 5/1997 | King et al. |
| 5,635,402 A | 6/1997 | Alfano et al. |
| 5,641,633 A | 6/1997 | Linn et al. |
| 5,645,800 A | 7/1997 | Masterson et al. |
| 5,663,545 A | 9/1997 | Marquiss |
| 5,670,113 A | 9/1997 | Akong et al. |
| 5,672,880 A | 9/1997 | Kain |
| 5,676,943 A | 10/1997 | Baetge et al. |
| 5,677,196 A | 10/1997 | Herron et al. |
| 5,679,310 A | 10/1997 | Manns |
| 5,736,410 A | 4/1998 | Zarling et al. |
| 5,738,825 A | 4/1998 | Rudigier et al. |
| 5,741,554 A | 4/1998 | Tisone |

| | | |
|---|---|---|
| 5,746,974 A | 5/1998 | Massey et al. |
| 5,750,410 A | 5/1998 | Dou et al. |
| 5,756,292 A | 5/1998 | Royer |
| 5,766,875 A | 6/1998 | Hafeman et al. |
| 5,780,857 A | 7/1998 | Harju et al. |
| 5,798,083 A | 8/1998 | Massey et al. |
| 5,798,085 A | 8/1998 | Seaton et al. |
| 5,825,617 A | 10/1998 | Kochis et al. |
| 5,842,582 A | 12/1998 | DeStefano, Jr. |
| 5,888,454 A | 3/1999 | Leistner et al. |
| 5,905,571 A | 5/1999 | Butler et al. |
| 5,933,232 A | 8/1999 | Atzler et al. |
| 5,959,738 A | 9/1999 | Hafeman et al. |
| 5,989,835 A | 11/1999 | Dunlay et al. |
| 5,993,746 A | 11/1999 | Priha et al. |
| 6,020,591 A | 2/2000 | Harter et al. |
| 6,025,985 A | 2/2000 | Leytes et al. |
| 6,033,100 A | 3/2000 | Marquiss et al. |
| 6,071,748 A | 6/2000 | Modlin et al. |
| 6,097,025 A | 8/2000 | Modlin et al. |
| 6,137,584 A | 10/2000 | Seidel et al. |
| 6,159,425 A | 12/2000 | Edwards et al. |
| 6,187,267 B1 | 2/2001 | Taylor et al. |

FOREIGN PATENT DOCUMENTS

| | | |
|---|---|---|
| EP | 0 993 916 A2 | 10/1999 |
| EP | 0 995 555 A1 | 10/1999 |
| EP | 1 003 020 A1 | 5/2000 |
| EP | 1 003 039 A1 | 5/2000 |
| GB | 2228081 | 8/1990 |
| GB | 2215838 | 9/1990 |
| WO | WO99/04288 | 1/1999 |
| WO | WO99/08233 | 2/1999 |
| WO | WO99/23466 | 5/1999 |
| WO | WO99/37203 | 7/1999 |
| WO | WO99/42817 | 8/1999 |
| WO | WO99/54711 | 10/1999 |
| WO | WO00/04364 | 1/2000 |
| WO | WO00/06989 | 2/2000 |
| WO | WO00/06990 | 2/2000 |
| WO | WO00/06991 | 2/2000 |
| WO | WO00/42209 | 7/2000 |
| WO | WO00/50877 | 8/2000 |
| WO | WO00/55372 | 9/2000 |
| WO | WO00/66269 | 11/2000 |
| WO | WO01/04608 | 1/2001 |

OTHER PUBLICATIONS

*Basic Fluorescence Microscopy*, Taylor et al., *Methods in Cell Biology*, vol. 29, pp. 207–237, 1989.
*Quantitative Fluorescence Microscopy Using Photomultiplier Tubes and Imaging Detectors*, Wampler et al., *Methods in Cell Biology*, vol. 30, pp. 239–267, 1989.
*Three–Dimensional Confocal Fluorescence Microscopy*, Brakenhoff et al., *Methods in Cell Biology*, vol. 30, pp. 379–389, 1989.
*Laser Scanning Confocal Microscopy of Living Cells*, Lemasters et al., *Optical Microscopy: Emerging Methods and Applications*, pp. 339–345, 1993.
*Time–Resolved Fluorescence Lifetime Imaging*, vande Ven et al., *Optical Microscopy: Emerging Methods and Applications*, pp. 373–389,1993.
*Electrochemiluminescence: A New Diagnostic and Research Tool*, Yang et al., *Bio/Technology*, vol. 12, pp. 193–194, Feb. 1994.
*Sorting Single Molecules: Application to Diagnostics and Evolutionary Biotechnology*, Eigen et al., *PNAS*, vol. 91, pp. 5740–5747, 1994.

*High Throughput Screening Using Dynamic Fluorescence*, Swift et al., *SPIE*, vol. 2388, pp. 182–189, Feb. 6–8, 1995.
Genesis Series Robotic Sample Processors brochure, Tecan AG, Oct. 1997.
Genesis Robotic Microprocessor brochure, Tecan AG, Nov. 1997.
A Measure of Brilliance, TR717 Microplate Luminometer brochure, Tropix, Inc., 1997.
Advanced Microplate Detection Systems brochure, Tecan AG, Feb. 1998.
The SPECTRA Family brochure, Tecan AG, Feb. 1998.
Assist Plate Handlind Device brochure, Labsystems, May 1998.
Wallac Time–Resolved Fluorometry—The Key to Improved Assay Sensitivity, internet description pages, Jul. 7, 1998.
Wallac 1234 DELFIA Fluorometer, internet description page, Jul. 7, 1998.
Wallac 1420 VICTOR Multilabel Counter, internet description pages, Jul. 7, 1998.
Wallac 1420 VICTOR$^2$ Multilabel Counter, internet description pages, Jul. 7, 1998.
Wallac 1442 ARTHUR Multi–Wavelength Fluoroimager, internet description page, Jul. 7, 1998.
Wallac Labeling Reagents for Time–Resolved Fluorometry, internet description pages, Jul. 7, 1998.
Genesis Assay Workstation brochure, Tecan AG, Jul. 1998.
Genesis Logistics Workstation brochure, Tecan AG, Jul. 1998.
Polarion brochure, Tecan AG, Aug. 1998.
CytoFluor Fluorescence Multi–Well Plate Reader brochure, PerSeptive Biosystems, 1998.
Microplate Instrumentation Catalogue 1998, Labsystems, 1998.
*Fixed Polarizer Ellipsometry for Simple and Sensitive Detection of Thin Films Generated by Specific Molecular Interactions: Applications in Immunoassays and DNA Sequence Detection*, Ostroff et al., *Clinical Chemistry*, 44:9, pp. 2031–2035, 1998.
Magellan, Instrument Control and Data Analysis Software brochure, Tecan AG, Nov. 1999.
TWISTER™, Tecan's Automated Microplate Handler brochure, Tecan AG, Nov. 1999.
*A Microfabricated Fluorescence–Activated Cell Sorter*, Fu et al., *Nature Biotechnology*, vol. 17, pp. 1109–1111, Nov. 1999.
Absorbance Readers brochure, Tecan AG, Dec. 1999.
Ultra—The Solution for HTS and Assay Development brochure, Tecan Austria GMBH, Dec. 1999.
*Principles of Fluorescence Spectroscopy*, Joseph R. Lakowicz, Second Edition, 1999.
CyBi™–Lumax 1,536 brochure, CyBio AG, May 2000.
CyBi™–PlateSafe brochure, CyBio AG, May 2000.
SPECTRAmax® Gemini XS brochure, Molecular Devices Corp., Jun. 2000.
SPECTRAmax® PLUS$^{384}$ brochure, Molecular Devices Corp., Jun. 2000.
Packard BioScience Company Introduces the Fusion™ Universal Microplate Analyzer press release, Packard BioScience Company, Jun. 29, 2000.
Labcyte: Research and Clinical Instruments for Life Sciences brochure, Arlena Research LLC, Aug. 1, 2000.
Fusion™ Universal Microplate Analyzer, Packard BioScience Company, Aug. 2000.

CyBi™–Screen–Machine: One System–Many Solutions brochure, CyBio AG, 2000.

Acumen Explorer brochure, Acumen, undated.

FLIPR 384: Essential Technology for Drug Discovery brochure, Molecular Devices Corp., undated.

FLUOstar Galaxey brochure, BMG Labtechnologies GmbH, undated.

NEPHELOstar brochure, BMG Labtechnologies GmbH, undated.

LUMIstar Galaxy brochure, BMG Labtechnologies GmbH, undated.

POLARstar Galaxy brochure, BMG Labtechnologies GmbH, undated.

POLARstar Galaxy flyer, BMG Labtechnologies GmbH, undated.

* cited by examiner

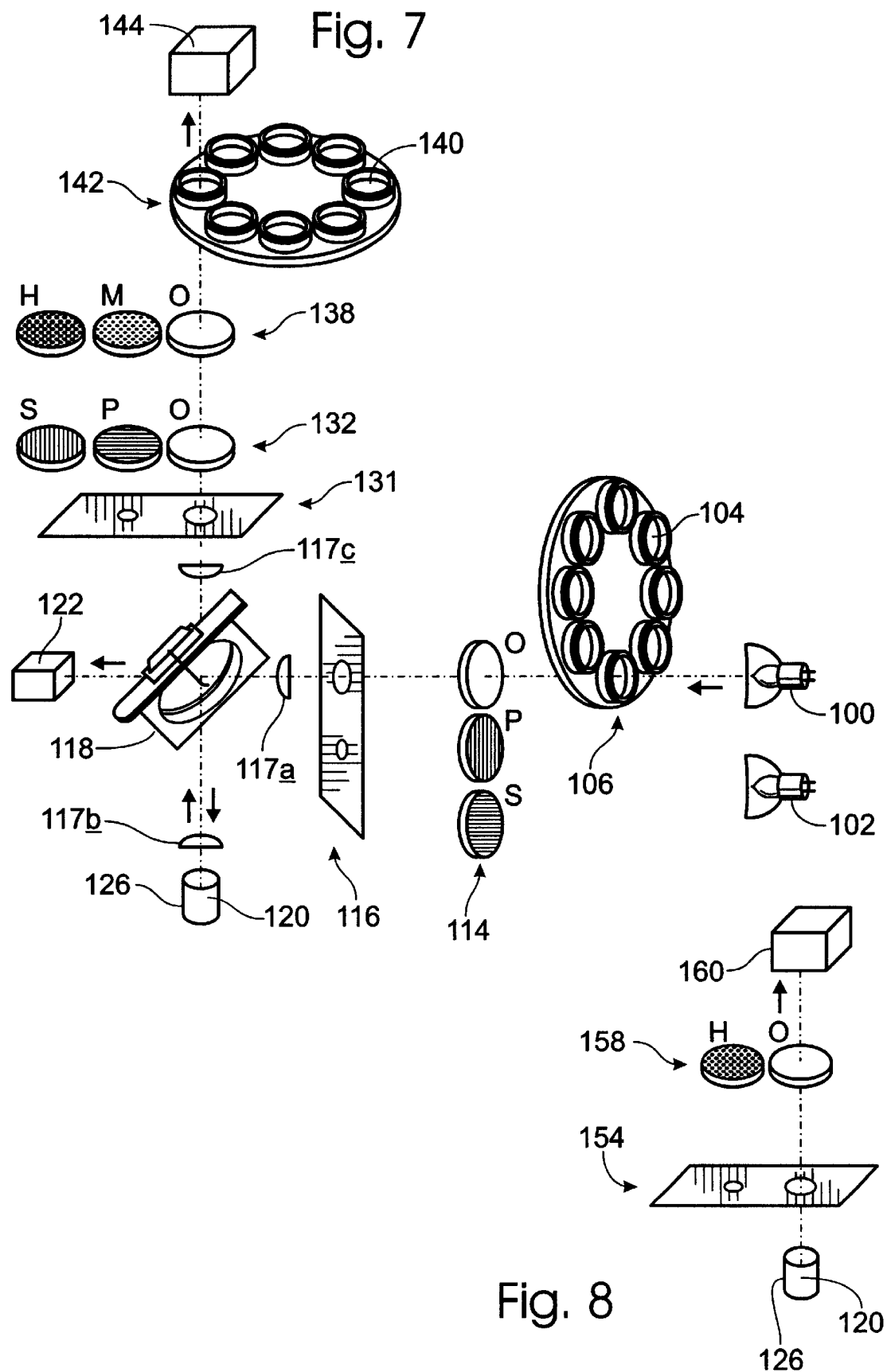

APPARATUS AND METHODS FOR TIME-RESOLVED SPECTROSCOPIC MEASUREMENTS

CROSS-REFERENCES TO PRIORITY APPLICATIONS

This application is a continuation of PCT patent application Ser. No. PCT/US99/16287, filed Jul. 26, 1999, which in turn claims priority from U.S. Provisional Patent Application Ser. No. 60/094,276, filed Jul. 27, 1998. These PCT and provisional applications are each incorporated herein by reference.

CROSS-REFERENCES TO RELATED MATERIALS

This application incorporates by reference the following U.S. patent applications: Ser. No. 09/156,318, filed Sep. 18, 1998; and Ser. No. 09/349,733, filed Jul. 8, 1999.

This application also incorporates by reference the following PCT patent applications: Ser. No. PCT/US98/23095, filed Oct. 30, 1998; Ser. No. PCT/US99/01656, filed Jan. 25, 1999; Ser. No. PCT/US99/03678, filed Feb. 19, 1999; Ser. No. PCT/US99/08410, filed Apr. 16, 1999; Ser. No. PCT/US99/16057, filed Jul. 15, 1999; Ser. No. PCT/US99/16453, filed Jul. 21, 1999; Ser. No. PCT/US99/16621, filed Jul. 23, 1999; and Ser. No. PCT/US99/16286, filed Jul. 26, 1999.

This application also incorporates by reference the following U.S. provisional patent applications: Ser. No. 60/100,817, filed Sep. 18, 1998; Ser. No. 60/100,951, filed Sep. 18, 1998; Ser. No. 60/104,964, filed Oct. 20, 1998; Ser. No. 60/114,209, filed Dec. 29, 1998; Ser. No. 60/116,113, filed Jan. 15, 1999; Ser. No. 60/117,278, filed Jan. 26, 1999; Ser. No. 60/119,884, filed Feb. 12, 1999; Ser. No. 60/121,229, filed Feb. 23, 1999; Ser. No. 60/124,686, filed Mar. 16, 1999; Ser. No. 60/125,346, filed Mar. 19, 1999; Ser. No. 60/126,661, filed Mar. 29, 1999; Ser. No. 60/130,149, filed Apr. 20, 1999; Ser. No. 60/132,262, filed May 3, 1999; Ser. No. 60/132,263, filed May 3, 1999; Ser. No. 60/135,284, filed May 21, 1999; Ser. No. 60/138,311, filed Jun. 9, 1999; Ser. No. 60/138,438, filed Jun. 10, 1999; Ser. No. 60/138,737, filed Jun. 11, 1999; Ser. No. 60/138,893, filed Jun. 11, 1999; and Ser. No. 60/142,721, filed Jul. 7, 1999.

This application also incorporates by reference the following publications: Max Born and Emil Wolf, *Principles of Optics* (6th ed. 1980); Richard P. Haugland, *Handbook of Fluorescent Probes and Research Chemicals* (6th ed. 1996); and Joseph R. Lakowicz, *Principles of Fluorescence Spectroscopy* (1983).

FIELD OF THE INVENTION

The invention relates to time-resolved spectroscopic assays. More particularly, the invention relates to apparatus and methods for conducting frequency-domain time-resolved spectroscopic measurements of luminescence lifetimes and/or reorientational correlation times.

BACKGROUND OVERVIEW OF SPECTROSCOPIC ASSAYS

Generally speaking, spectroscopy involves the study of matter using electromagnetic radiation. Spectroscopic measurements can be separated into three broad categories: absorbance, scattering/reflectance, and emission. Absorbance assays involve relating the amount of incident light that is absorbed by a sample to the type and number of molecules in the sample. Absorbance assays are a powerful method for determining the presence and concentration of an analyte in a sample. Most commonly, absorbance is measured indirectly by studying the portion of incident light that is transmitted by the sample. Scattering assays are similar to absorbance in that the measurement is based on the amount of incident light which emerges or is transmitted from the sample. However, in the case of scattering, the signal increases with the number of interactions, whereas, in the case of absorbance, the signal is inversely proportional to the interactions. Emission assays look at electromagnetic emissions from a sample other than the incident light. In each case, the measurements may be broad spectrum or wavelength specific depending on the particular assay.

1. Absorbance Assays

FIG. 1 shows a schematic view of a typical absorbance experiment. Generally, absorbance measurements are made by directing incident light from a light source through a sample and through two walls of a sample container, and measuring the transmitted light using a detector. Unfortunately, this approach has a number of shortcomings. In particular, the sample container may absorb part or all of the incident and transmitted light, decreasing or eliminating the sample signal and increasing the background signal. Moreover, correcting for absorbance by the sample container requires the performance of two experiments, one involving the sample and sample container, and the other involving only the sample container.

The amount of light absorbed by a sample in an absorbance experiment generally may be described by the Beer-Lambert law: Absorbance =−log $$\text{Absorbance} = -\log\left(\frac{I(\lambda)}{I_0(\lambda)}\right) = \varepsilon(\lambda)cl \qquad (1)$$

The Beer-Lambert law states that when light of wavelength λ passes through an absorbing sample, its intensity, I, decreases exponentially. Here, $I_0(\lambda)$ is the intensity of the incident light at wavelength λ, $I(\lambda)$ is the intensity of the transmitted light, $\varepsilon(\lambda)$ is the decadic molar extinction coefficient, c is the concentration of absorbing molecules, and 1 is the path length. The quantity $-\log(I/I_0)$ is termed the absorbance and is the logarithm of the reciprocal of the fraction of transmitted light.

Generally, absorbance measurements are most accurate when the absorbance is in the range 0.1–2.0, corresponding to absorption of about 20–99% of the incident light. Yet, in many biological and pharmaceutical applications, such "high" absorbances may be difficult to obtain, because the absorbing molecules may be expensive and/or available in small quantities. Moreover, in many biological and pharmaceutical applications, small samples are desirable, because experimental procedures may involve studying hundreds of thousands of samples, such that small samples decrease reagent costs and the overall space required.

As seen from Equation 1, absorbance may be increased by increasing the concentration of absorbing molecules. Unfortunately, this approach has a number of shortcomings. In particular, because concentration is the number of molecules per unit volume, increasing the concentration involves increasing the number of molecules and/or decreasing the volume. Yet, increasing the number of molecules is undesirable if the molecules are expensive and/or rare. Similarly, decreasing the volume is undesirable because it may decrease the path length and so decrease absorbance.

Also as seen from Equation 1, absorbance may be increased by increasing the path length. Unfortunately, this approach also has a number of shortcomings. In particular, increasing the path length may involve increasing the volume of sample, and hence increasing the number of molecules and the overall space required. Alternatively, increasing the path length may involve decreasing the cross section of the sample, decreasing signal.

2. Scattering Assays

Scattering assays can be used to detect the motion, size, concentration, aggregation state, and other properties of molecules in a sample. For example, by looking at the spectral spread of scattered light, it is possible to determine the average velocity of scattering particles in a sample. By observing the intensity of scattered light, the concentration of scattering objects can be measured. By observing the angular distribution of scattered light, various physical characteristics of scattering molecules can be deduced.

3. Luminescence Assays

Luminescence is the emission of light from excited electronic states of atoms or molecules. Luminescence generally refers to all kinds of light emission, except incandescence, and may include photoluminescence, chemiluminescence, and electrochemiluminescence, among others. In photoluminescence, including fluorescence and phosphorescence, the excited electronic state is created by the absorption of electromagnetic radiation. In chemiluminescence, which includes bioluminescence, the excited electronic state is created by a transfer of chemical energy. In electrochemiluminescence, the excited electronic state is created by an electrochemical process.

Luminescence assays are assays that use luminescence emissions from luminescent analytes to study the properties and environment of the analyte, as well as binding reactions and enzymatic activities involving the analyte, among others. In this sense, the analyte may act as a reporter to provide information about another material or target substance that may be the focus of the assay. Luminescence assays may use various aspects of the luminescence, including its intensity, polarization, and lifetime, among others. Luminescence assays also may use time-independent (steady-state) and/or time-dependent (time-resolved) properties of the luminescence. Steady-state assays generally are less complicated than time-resolved assays, but generally yield less information.

A. Intensity Assays

Luminescence intensity assays involve monitoring the intensity (or amount) of light emitted from a composition. The intensity of emitted light will depend on the extinction coefficient, quantum yield, and number of the luminescent analytes in the composition, among others. These quantities, in turn, will depend on the environment of the analyte, among others, including the proximity and efficacy of quenchers and energy transfer partners. Thus, luminescence intensity assays may be used to study binding reactions, among other applications.

B. Polarization Assays

Luminescence polarization assays involve the absorption and emission of polarized light, and typically are used to study molecular rotation. (Polarization describes the direction of light's electric field, which generally is perpendicular to the direction of light's propagation.)

FIG. 2 is a schematic view showing how luminescence polarization is affected by molecular rotation. In a luminescence polarization assay, specific molecules 30 within a composition 32 are labeled with one or more luminophores.

The composition then is illuminated with polarized excitation light, which preferentially excites luminophores having absorption dipoles aligned parallel to the polarization of the excitation light. These molecules subsequently decay by preferentially emitting light polarized parallel to their emission dipoles. The extent to which the total emitted light is polarized depends on the extent of molecular reorientation during the time interval between luminescence excitation and emission, which is termed the luminescence lifetime, $\tau$. The extent of molecular reorientation in turn depends on the luminescence lifetime and the size, shape, and environment of the reorienting molecule. Thus, luminescence polarization assays may be used to quantify binding reactions and enzymatic activity, among other applications. In particular, molecules commonly rotate via diffusion with a rotational correlation time $\tau_{rot}$ that is proportional to their size. Thus, during their luminescence lifetime, relatively large molecules will not reorient significantly, so that their total luminescence will be relatively polarized. In contrast, during the same time interval, relatively small molecules will reorient significantly, so that their total luminescence will be relatively unpolarized.

The relationship between polarization and intensity is expressed by the following equation:

$$P = \frac{I_{\|} - I_{\perp}}{I_{\|} + I_{\perp}} \tag{2}$$

Here, P is the polarization, $I_{\|}$ is the intensity of luminescence polarized parallel to the polarization of the excitation light, and $I_{\perp}$ is the intensity of luminescence polarized perpendicular to the polarization of the excitation light. P generally varies from zero to one-half for randomly oriented molecules (and zero to one for aligned molecules). If there is little rotation between excitation and emission, $I_{\|}$ will be relatively large, $I_{\perp}$ will be relatively small, and P will be close to one-half. (P may be less than one-half even if there is no rotation; for example, P will be less than one if the absorption and emission dipoles are not parallel.) In contrast, if there is significant rotation between absorption and emission, $I_{\|}$ will be comparable to $I_{\perp}$, and P will be close to zero. Polarization often is reported in milli-P (mP) units (1000×P), which for randomly oriented molecules will range between 0 and 500, because P will range between zero and one-half.

Polarization also may be described using other equivalent quantities, such as anisotropy. The relationship between anisotropy and intensity is expressed by the following equation:

$$r = \frac{I_{\|} - I_{\perp}}{I_{\|} + 2I_{\perp}} \tag{3}$$

Here, r is the anisotropy. Polarization and anisotropy include the same information, although anisotropy may be more simply expressed for systems containing more than one luminophore. In the description and claims that follow, these terms may be used interchangeably, and a generic reference to one should be understood to imply a generic reference to the other.

The relationship between polarization, luminescence lifetime, and rotational correlation is expressed by the Perrin equation:

$$\left(\frac{1}{P} - \frac{1}{3}\right) = \left(\frac{1}{P_0} - \frac{1}{3}\right) \cdot \left(1 + \frac{\tau}{\tau_{rot}}\right) \quad (4)$$

Here, $P_0$ is the polarization in the absence of molecular motion (intrinsic polarization), $\tau$ is the luminescence lifetime (inverse decay rate) as described above, and $\tau_{rot}$ is the rotational correlation time (inverse rotational rate) as described above.

The Perrin equation shows that luminescence polarization assays are most sensitive when the luminescence lifetime and the rotational correlation time are similar. Rotational correlation time is proportional to molecular weight, increasing by about 1 nanosecond for each 2,400 Dalton increase in molecular weight (for a spherical molecule). For shorter lifetime luminophores, such as fluorescein, which has a luminescence lifetime of roughly 4 nanoseconds, luminescence polarization assays are most sensitive for molecular weights less than about 40,000 Daltons. For longer lifetime probes, such as Ru(bpy)$_2$dcbpy (ruthenium 2,2'-dibipyridyl 4,4'-dicarboxyl-2,2'-bipyridine), which has a lifetime of roughly 400 nanoseconds, luminescence polarization assays are most sensitive for molecular weights between about 70,000 Daltons and 4,000,000 Daltons.

C. Time-Resolved Assays

Time-resolved assays involve measuring the time course of luminescence emission. Time-resolved assays may be conducted in the time domain or in the frequency domain, both of which are functionally equivalent. In a time-domain measurement, the time course of luminescence is monitored directly. Typically, a composition containing a luminescent analyte is illuminated using a narrow pulse of light, and the time dependence of the intensity of the resulting luminescence emission is observed, although other protocols also may be used. For a simple molecule, the luminescence commonly follows a single-exponential decay.

In a frequency-domain measurement, the time course of luminescence is monitored indirectly, in frequency space. Typically, the composition is illuminated using light whose intensity is modulated sinusoidally at a single modulation frequency $f$, although other protocols (such as transforming time-domain data into the frequency domain) also may be used. The intensity of the resulting luminescence emission is modulated at the same frequency as the excitation light. However, the emission will lag the excitation by a phase angle (phase) $\phi$, and the intensity of the emission will be demodulated relative to the intensity of the excitation by a demodulation factor (modulation) M.

FIG. 3 shows the relationship between emission and excitation in a single-frequency frequency-domain experiment. The phase $\phi$ is the phase difference between the excitation and emission. The modulation M is the ratio of the AC amplitude to the DC offset for the emission, relative to the ratio of the AC amplitude to the DC offset for the excitation. The phase and modulation are related to the luminescence lifetime $\tau$ by the following equations:

$$\omega\tau = \tan(\phi) \quad (5)$$

$$\omega\tau = \sqrt{\frac{1}{M^2} - 1} \quad (6)$$

Here $\omega$ is the angular modulation frequency, which equals $2\pi$ times the modulation frequency. For maximum sensitivity, the angular modulation frequency should be roughly the inverse of the luminescence lifetime. Lifetimes of interest in high-throughput screening vary from less than 1 nanosecond to greater than 1 milliseconds. Therefore, instruments for high-throughput screening should be able to cover modulation frequencies from about 200 Hz to about 200 MHz.

D. Strengths and Weaknesses of Luminescence Assays

Luminescence methods have several significant potential strengths. First, luminescence methods may be very sensitive, because modem detectors, such as photomultiplier tubes (PMTs) and charge-coupled devices (CCDs), can detect very low levels of light. Second, luminescence methods may be very selective, because the luminescence signal may come almost exclusively from the luminophore.

Luminescence assays also have several significant potential weaknesses. First, luminescence from the analyte might be perturbed in some way, distorting results. For example, if a luminescent analyte binds to the walls of a sample holder during a luminescence polarization assay, the analyte will be unable to rotate, spuriously increasing the polarization. Second, luminescence may arise from sources other than the analyte, contaminating the signal. For example, luminescence may arise from the sample holder, including glass coverslips and plastic microplates.

BRIEF DESCRIPTION OF THE DRAWINGS

FIG. 7 is a schematic view of photoluminescence optical components from the apparatus of FIG. 5.

FIG. 8 is a schematic view of chemiluminescence optical components from the apparatus of FIG. 5.

DETAILED DESCRIPITON OF THE INVENTION

The detailed description is divided into five parts: (1) description of a spectroscopic apparatus, (2) luminescence assays, (3) enhancement of signal, (4) absorbance assays, and (5) scattering assays.

1. Description of Apparatus

Figure 1:
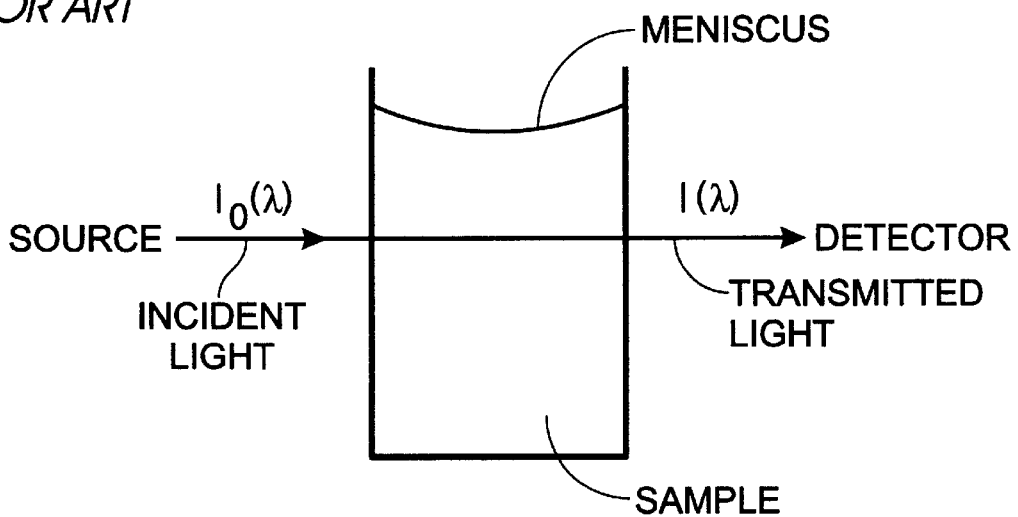
FIG. 1 is a schematic view of a typical absorbance experiment.
Figure 2:
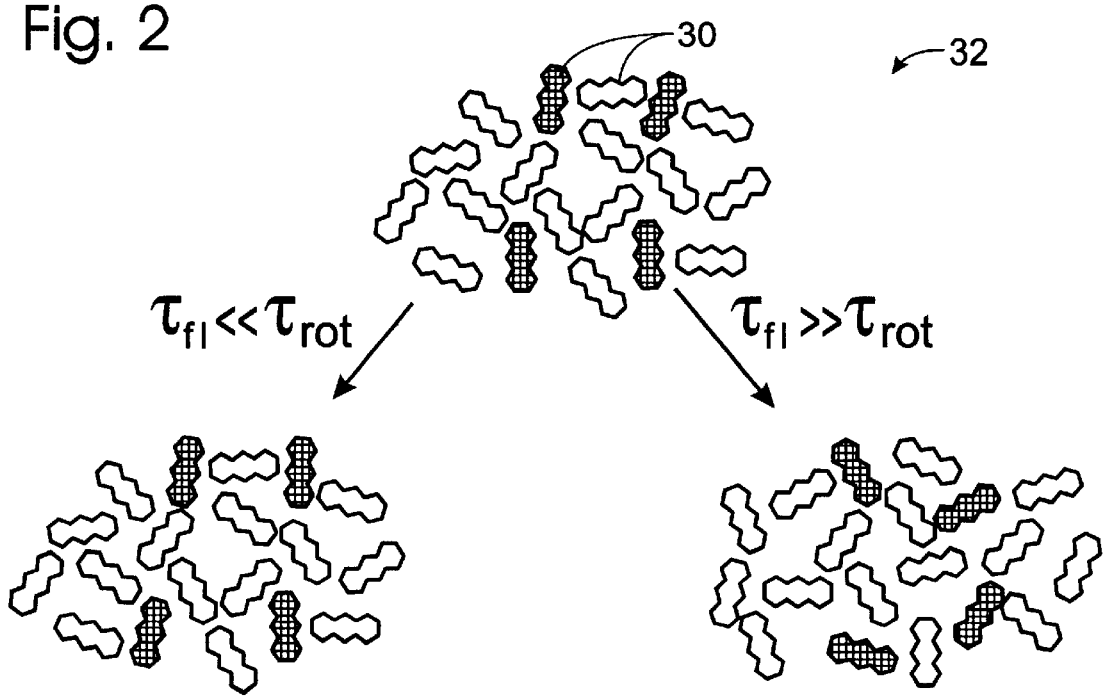
FIG. 2 is a schematic view of luminescently labeled molecules, showing how molecular reorientation affects luminescence polarization.
Figure 3:
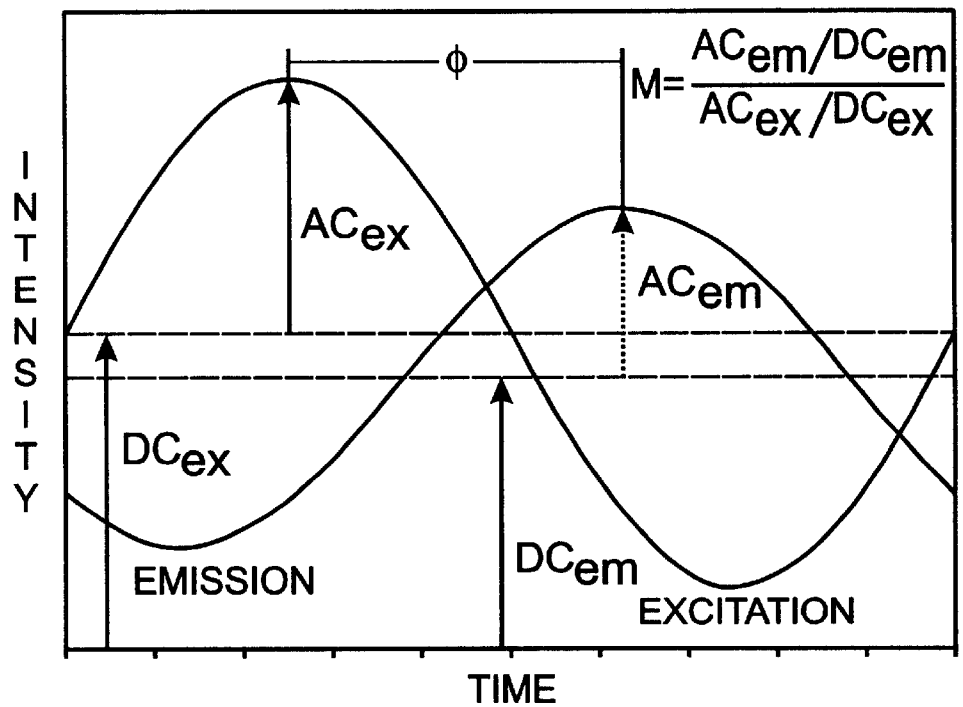
FIG. 3 is a schematic view of a frequency-domain time-resolved measurement, showing the definitions of phase angle (phase) $\phi$ and demodulation factor (modulation) M.
Figure 4:
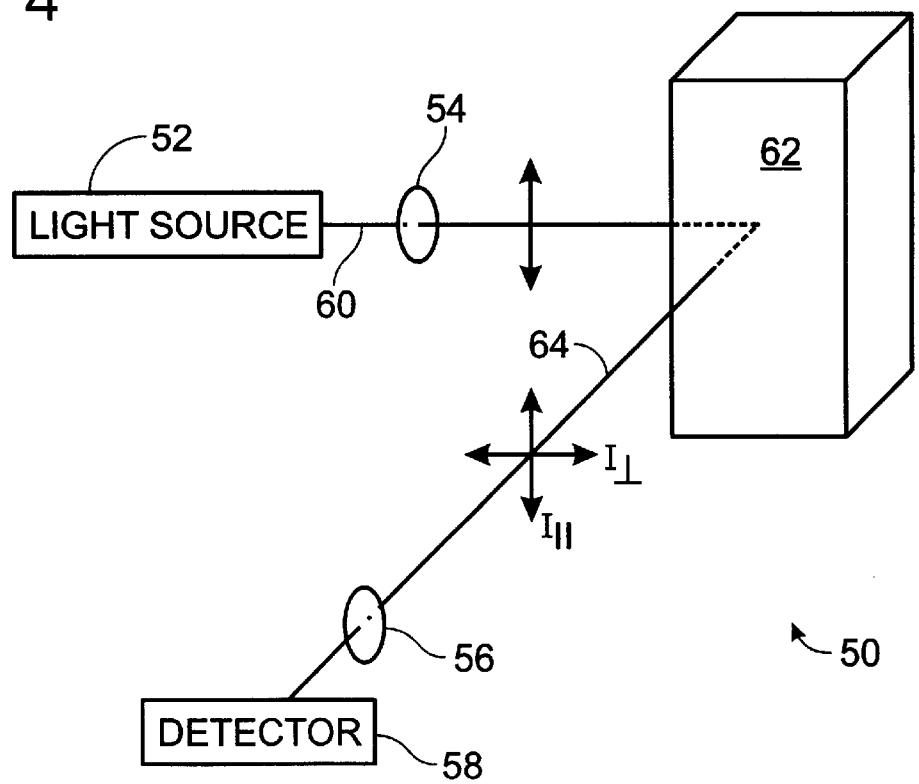
FIG. 4 is a schematic view of an apparatus for detecting light in accordance with the invention.

FIG. 4 shows an apparatus 50 for detecting light (including polarized light) leaving a sample. Apparatus 50 includes a light source 52, an excitation polarizer 54, an emission polarizer 56, and a detector 58. Light 60 produced by light source 52 is directed through excitation polarizer 54, which passes polarized excitation light (indicated by vertical arrow). Polarized excitation light is directed onto a sample 62, which emits light 64 in response. The emitted light may be either some fraction of the incident light or luminescence. Emitted light 64 is directed through emission polarizer 56, which may have components oriented parallel ($\|$; indicated by vertical arrow) or perpendicular ($\perp$; indicated by horizontal arrow) to the polarization of excitation light 60. Depending on its orientation, emission polarizer 56 passes parallel ($I_\|$) or perpendicular ($I_\perp$) components of emission light 64 for detection by detector 58.

FIGS. 5–8 show an alternative apparatus 90 for detecting light emitted by an analyte in a composition. Apparatus 90 includes (1) a stage for supporting the composition, (2) one or more light sources for delivering light to a composition, (3) one or more detectors for receiving light transmitted from the composition and converting it to a signal, (4) first and second optical relay structures for relaying light between the light source, composition, and detector, and (5) a processor for analyzing the signal from the detector. All or only a subset of these components may be used in any given application.

Apparatus 90 may be used for a variety of assays, including but not limited to the assays described above. Components of the optical system may be chosen to optimize sensitivity and dynamic range for each assay supported by the apparatus. Toward this end, optical components with low intrinsic luminescence are preferred. In addition, some components may be shared by different modes, whereas other components may be unique to a particular mode. For example, in apparatus 90, absorbance, scattering, photoluminescence intensity and steady-state photoluminescence polarization modes share a light source; time-resolved absorbance and luminescence modes use their own light source; and chemiluminescence modes do not use a light source. Similarly, photoluminescence and chemiluminescence modes use different detectors.

The remainder of this section is divided into four subsections: (A) incident light-based optical system, (B) chemiluminescence optical system, (C) housing, and (D) frequency-domain detection system.

A. Incident Light-Based Optical System

FIGS. 8–13 show the incident light-based optical system of apparatus 90. As configured here, apparatus 90 includes a continuous light source 100 and a time-modulated light source 102. Apparatus 90 includes light source slots 103a–d for four light sources, although other numbers of light sources and light sources also could be provided. Light source slots 103a–d function as housings that may surround at least a portion of each light source, providing some protection from radiation and explosion. The direction of light transmission through the incident light-based optical system is indicated by arrows.

Continuous source 100 provides light for absorbance, scattering, photoluminescence intensity, and steady-state photoluminescence polarization assays. Continuous light source 100 may include arc lamps, incandescent lamps, fluorescent lamps, electroluminescent devices, lasers, laser diodes, and light-emitting diodes (LEDs), among others. A preferred continuous source is a high-intensity, high color temperature xenon arc lamp, such as a Model LX175F CERMAX xenon lamp from ILC Technology, Inc. Color temperature is the absolute temperature in Kelvin at which a blackbody radiator must be operated to have a chromaticity equal to that of the light source. A high color temperature lamp produces more visible light than a low color temperature lamp, and it may have a maximum output shifted toward or into visible wavelengths and ultraviolet wavelengths where many luminophores absorb. The preferred continuous source has a color temperature of 5600 Kelvin, greatly exceeding the color temperature of about 3000 Kelvin for a tungsten filament source. The preferred source provides more light per unit time than flash sources, averaged over the flash source duty cycle, increasing sensitivity and reducing read times. Apparatus 90 may include a modulator mechanism configured to vary the intensity of light incident on the composition without varying the intensity of light produced by the light source.

Time-modulated source 102 provides light for time-resolved absorbance and/or photoluminescence assays, such as photoluminescence lifetime and time-resolved photoluminescence polarization assays. A preferred time-modulated source is a xenon flash lamp, such as a Model FX-1160 xenon flash lamp from EG&G Electro-Optics. The preferred source produces a "flash" of light for a brief interval before signal detection and is especially well suited for time-domain measurements. Other time-modulated sources include pulsed lasers, electronically modulated lasers and LEDs, and continuous lamps and other sources whose intensity can be modulated extrinsically using a Pockels cell, Kerr cell, or other mechanism. Such other mechanisms may include an amplitude modulator such as a chopper as described in U.S. Provisional patent application No. 60/094, 276, which is incorporated herein by reference. Extrinsically modulated continuous light sources are especially well suited for frequency-domain measurements.

In apparatus 90, continuous source 100 and time-modulated source 102 produce multichromatic, unpolarized, and incoherent light. Continuous source 100 produces substantially continuous illumination, whereas time-modulated source 102 produces time-modulated illumination. Light from these light sources may be delivered to the sample without modification, or it may be filtered to alter its intensity, spectrum, polarization, or other properties.

Light produced by the light sources follows an excitation optical path to an examination site or measurement region. Such light may pass through one or more "spectral filters," which generally comprise any mechanism for altering the spectrum of light that is delivered to the sample. Spectrum refers to the wavelength composition of light. A spectral filter may be used to convert white or multichromatic light, which includes light of many colors, into red, blue, green, or other substantially monochromatic light, which includes light of one or only a few colors. In apparatus 90, spectrum is altered by an excitation interference filter 104, which preferentially transmits light of preselected wavelengths and preferentially absorbs light of other wavelengths. For convenience, excitation interference filters 104 gmay be housed in an excitation filter wheel 106, which allows the spectrum of excitation light to be changed by rotating a preselected filter into the optical path. Spectral filters also may separate light spatially by wavelength. Examples include gratings, monochromators, and prisms.

Spectral filters are not required for monochromatic ("single color") light sources, such as certain lasers, which output light of only a single wavelength. Therefore, excitation filter wheel 106 may be mounted in the optical path of some light source slots 103a,b, but not other light source slots 103c,d. Alternatively, the filter wheel may include a blank station that does not affect light passage.

Light next passes through an excitation optical shuttle (or switch) 108, which positions an excitation fiber optic cable 110a,b in front of the appropriate light source to deliver light to top or bottom optics heads 112a,b, respectively. Light is transmitted through a fiber optic cable much like water is transmitted through a garden hose. Fiber optic cables can be used easily to turn light around corners and to route light around opaque components of the apparatus. Moreover, fiber optic cables give the light a more uniform intensity profile. A preferred fiber optic cable is a fused silicon bundle, which has low autoluminescence. Despite these advantages, light also can be delivered to the optics heads using other mechanisms, such as mirrors.

Light arriving at the optics head may pass through one or more excitation "polarization filters," which generally comprise any mechanism for altering the polarization of light. Excitation polarization filters may be included with the top and/or bottom optics head. In apparatus 90, polarization is altered by excitation polarizers 114, which are included only with top optics head 112a for top reading; however, such polarizers also can be included with bottom optics head 112b for bottom reading. Excitation polarization filters 114 may include an s-polarizer S that passes only s-polarized light, a p-polarizer P that passes only p-polarized light, and a blank O that passes substantially all light. Excitation polarizers 114 also may include a standard or ferro-electric liquid crystal display (LCD) polarization switching system. Such a system may be faster than a mechanical switcher. Excitation polarizers 114 also may include a continuous mode LCD polarization rotator with synchronous detection to increase the signal-to-noise ratio in polarization assays. Excitation polarizers 114 may be incorporated as an inherent component in some light sources, such as certain lasers, that intrinsically produce polarized light.

Light at one or both optics heads also may pass through an excitation "confocal optics element," which generally comprises any mechanism for focusing light into a "sensed volume." In apparatus 90, the confocal optics element includes a set of lenses 117a–c and an excitation aperture 116 placed in an image plane conjugate to the sensed volume, as shown in FIG. 7. Aperture 116 may be implemented directly, as an aperture, or indirectly, as the end of a fiber optic cable. Preferred apertures have diameters of 1 mm and 1.5 mm. Lenses 117a,b project an image of aperture 116 onto the sample, so that only a preselected or sensed volume of the sample is illuminated. The area of illumination will have a diameter corresponding to the diameter of the excitation aperture.

Light traveling through the optics heads is reflected and transmitted through a beamsplitter 118, which delivers reflected light to a composition 120 and transmitted light to a light monitor 122. Reflected and transmitted light both pass through lens 117b, which is operatively positioned between beamsplitter 118 and composition 120.

Beamsplitter 118 is used to direct excitation or incident light toward the sample and light monitor, and to direct light leaving the sample toward the detector. The beamsplitter is changeable, so that it may be optimized for different assay modes or compositions. If a large number or variety of photoactive molecules are to be studied, the beamsplitter must be able to accommodate light of many wavelengths; in this case, a "50:50" beamsplitter that reflects half and transmits half of the incident light independent of wavelength is optimal. Such a beamsplitter can be used with many types of molecules, while still delivering considerable excitation light onto the composition, and while still transmitting considerable light leaving the sample to the detector. If one or a few related photoactive molecules are to be studied, the beamsplitter needs only to be able to accommodate light at a limited number of wavelengths; in this case, a "dichroic" or "multichroic" beamsplitter is optimal. Such a beamsplitter can be designed with cutoff wavelengths for the appropriate sets of molecules and will reflect most or substantially all of the excitation and background light, while transmitting most or substantially all of the emission light in the case of luminescence. This is possible because the beamsplitter may have a reflectivity and transmissivity that varies with wavelength.

Light monitor 122 is used to correct for fluctuations in the intensity of light provided by the light sources. Such corrections may be performed by reporting detected intensities as a ratio over corresponding times of the luminescence intensity measured by the detector to the excitation light intensity measured by the light monitor. The light monitor also can be programmed to alert the user if the light source fails. A preferred light monitor is a silicon photodiode with a quartz window for low autoluminescence.

The composition (or sample) may be held in a sample holder supported by a stage 123. The composition can include compounds, mixtures, surfaces, solutions, emulsions, suspensions, cell cultures, fermentation cultures, cells, tissues, secretions, and/or derivatives and/or extracts thereof. Analysis of the composition may involve measuring the presence, concentration, or physical properties (including interactions) of a photoactive analyte in such a composition. Composition may refer to the contents of a single microplate well, or several microplate wells, depending on the assay. In some embodiments, such as a portable apparatus, the stage may be intrinsic to the instrument.

The sample holder can include microplates, biochips, or any array of samples in a known format. In apparatus 90, the preferred sample holder is a microplate 124, which includes a plurality of microplate wells 126 for holding compositions. Microplates are typically substantially rectangular holders that include a plurality of sample wells for holding a corresponding plurality of samples. These sample wells are normally cylindrical in shape although rectangular or other shaped wells are sometimes used. The sample wells are typically disposed in regular arrays. The "standard" microplate includes 96 cylindrical sample wells disposed in a 8×12 rectangular array on 9 millimeter centers.

The sensed volume typically has an hourglass shape, with a cone angle of about 25° and a minimum diameter ranging between 0.1 mm and 2.0 mm. For 96-well and 384-well microplates, a preferred minimum diameter is about 1.5 mm. For 1536-well microplates, a preferred minimum diameter is about 1.0 mm. The size and shape of the sample holder may be matched to the size and shape of the sensed volume, as described in PCT patent application Ser. No. PCT/US99/08410, which is incorporated herein by reference.

Figure 5:
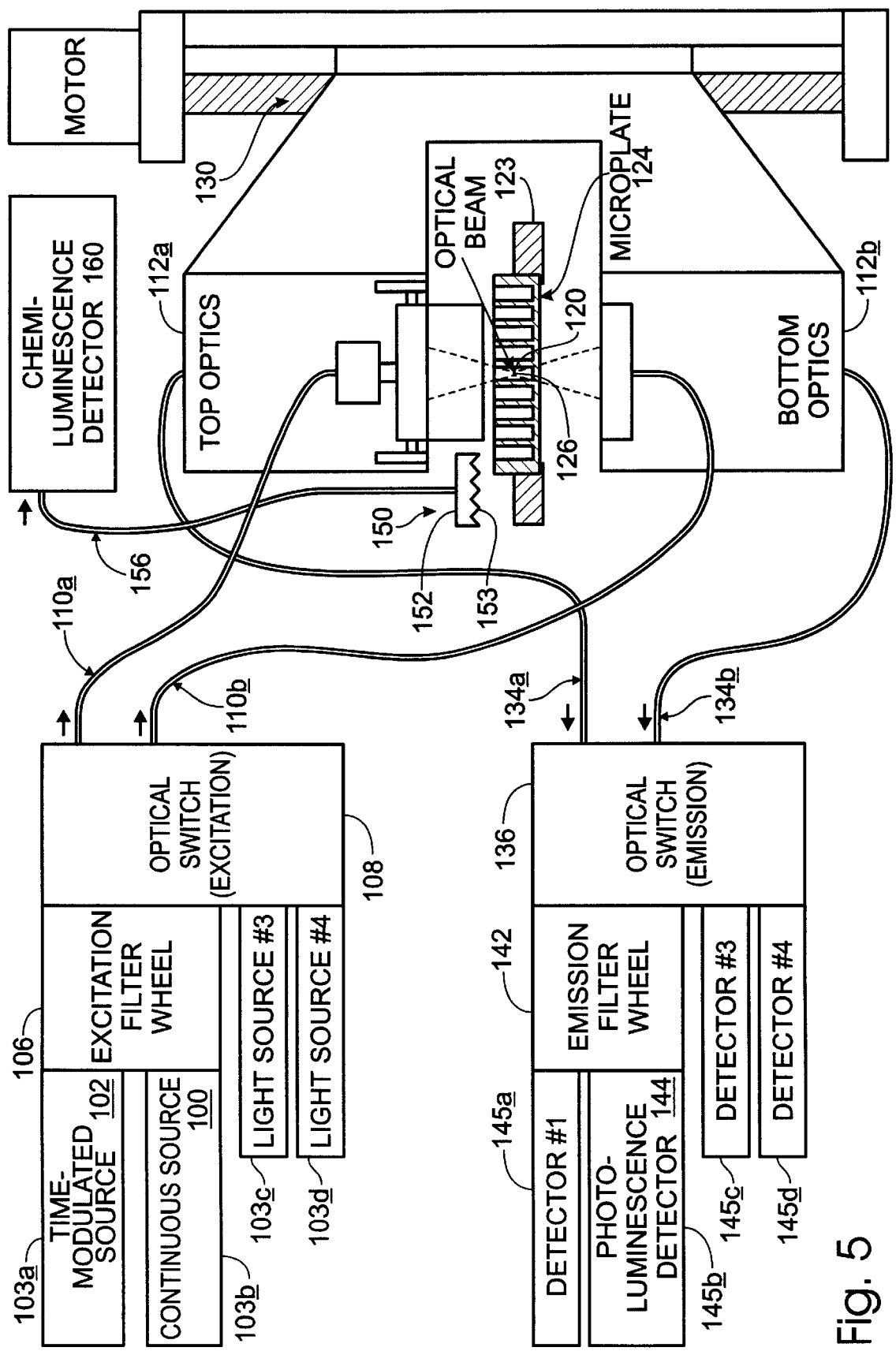
FIG. 5 is a schematic view of an alternative apparatus for detecting light in accordance with the invention.
Figure 6:
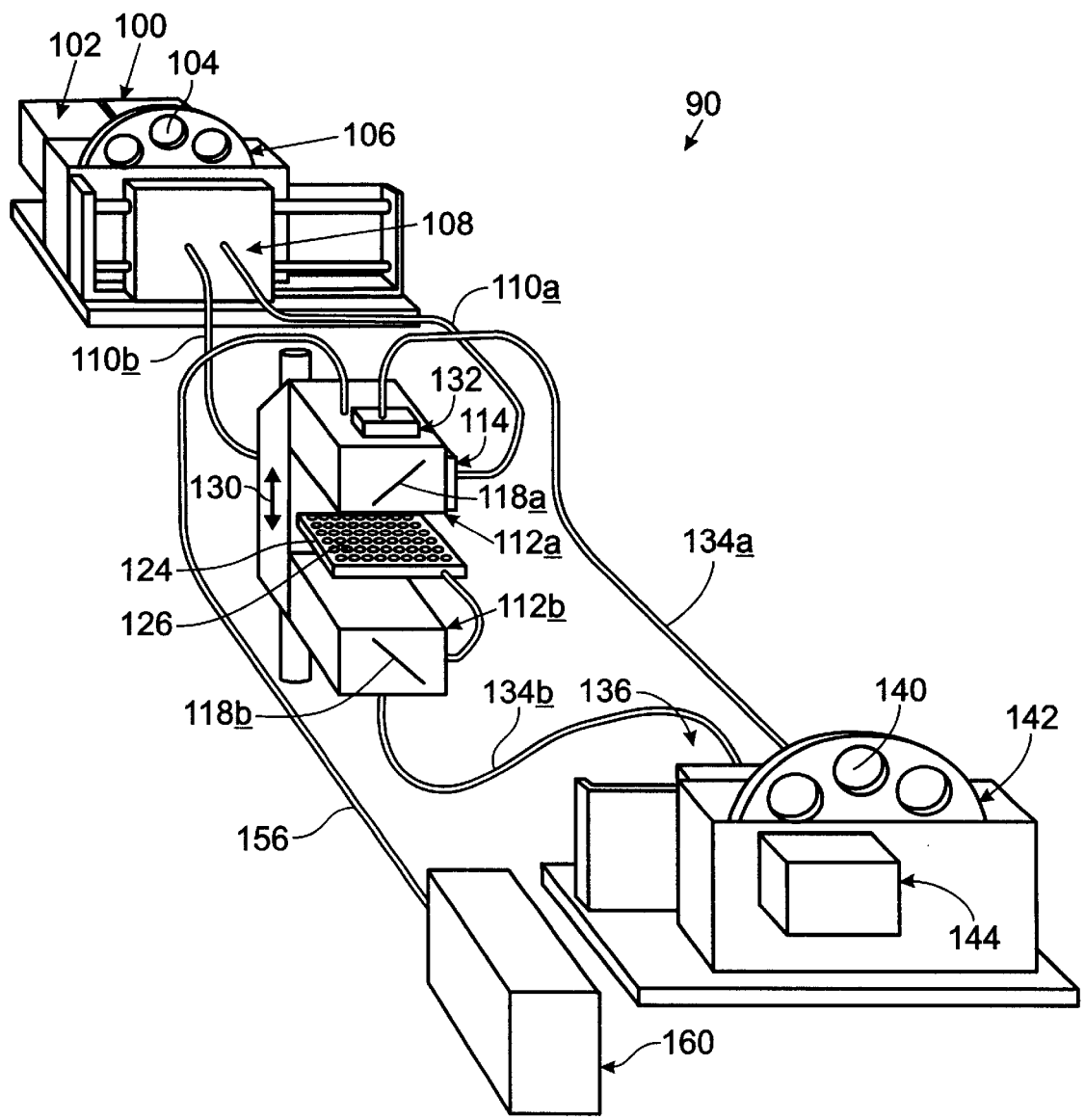
FIG. 6 is a partially schematic perspective view of the apparatus of FIG. 5.

The position of the sensed volume can be moved precisely within the composition to optimize the signal-to-noise and signal-to-background ratios. For example, the sensed volume may be moved away from walls in the sample holder to optimize signal-to-noise and signal-to-background ratios, reducing spurious signals that might arise from luminophores bound to the walls and thereby immobilized. In apparatus 90, position in the X,Y-plane perpendicular to the optical path is controlled by moving the stage supporting the composition, whereas position along the Z-axis parallel to the optical path is controlled by moving the optics heads using a Z-axis adjustment mechanism 130, as shown in FIGS. 5 and 6. However, any mechanism for bringing the sensed volume into register or alignment with the appropriate portion of the composition also may be employed.

The combination of top and bottom optics permits assays to combine: (1) top illumination and top detection, or (2) top illumination and bottom detection, or (3) bottom illumination and top detection, or (4) bottom illumination and bottom detection. Same-side illumination and detection, (1) and (4), is referred to as "epi" and is preferred for photoluminescence and scattering assays. Opposite-side illumination and detection, (2) and (3), is referred to as "trans" and has been used in the past for absorbance assays. In apparatus 90, epi modes are supported, so the excitation and emission light travel the same path in the optics head, albeit in opposite or anti-parallel directions. However, trans modes also can be used with additional sensors, as described below. In apparatus 90, top and bottom optics heads move together and share a common focal plane. However, in other embodiments, top and bottom optics heads may move independently, so that each can focus independently on the same or different sample planes.

Generally, top optics can be used with any sample holder having an open top, whereas bottom optics can be used only with sample holders having optically transparent bottoms, such as glass or thin plastic bottoms. Clear bottom sample holders are particularly suited for measurements involving analytes that accumulate on the bottom of the holder.

Light is transmitted by the composition in multiple directions. A portion of the transmitted light will follow an emission pathway to a detector. Transmitted light passes through lens 117c and may pass through an emission aperture 131 and/or an emission polarizer 132. In apparatus 90, the emission aperture is placed in an image plane conjugate to the sensed volume and transmits light substantially exclusively from this sensed volume. In apparatus 90, the emission apertures in the top and bottom optical systems are the same size as the associated excitation apertures, although other sizes also may be used. The emission polarizers are included only with top optics head 112a. The emission aperture and emission polarizer are substantially similar to their excitation counterparts. Emission polarizer 132 may be included in detectors that intrinsically detect the polarization of light.

Excitation polarizers 114 and emission polarizers 132 may be used together in nonpolarization assays to reject certain background signals. Luminescence from the sample holder and from luminescent molecules adhered to the sample holder is expected to be polarized, because the rotational mobility of these molecules should be hindered. Such polarized background signals can be eliminated by "crossing" the excitation and emission polarizers, that is, setting the angle between their transmission axes at 90°. As described above, such polarized background signals also can be reduced by moving the sensed volume away from walls of the sample holder. To increase signal level, beamsplitter 118 should be optimized for reflection of one polarization and transmission of the other polarization. This method will work best where the luminescent molecules of interest emit relatively unpolarized light, as will be true for small luminescent molecules in solution.

Transmitted light next passes through an emission fiber optic cable 134a,b to an emission optical shuttle (or switch) 136. This shuttle positions the appropriate emission fiber optic cable in front of the appropriate detector. In apparatus 90, these components are substantially similar to their excitation counterparts, although other mechanisms also could be employed.

Light exiting the fiber optic cable next may pass through one or more emission "intensity filters," which generally comprise any mechanism for reducing the intensity of light. Intensity refers to the amount of light per unit area per unit time. In apparatus 90, intensity is altered by emission neutral density filters 138, which absorb light substantially independent of its wavelength, dissipating the absorbed energy as heat. Emission neutral density filters 138 may include a high-density filter H that absorbs most incident light, a medium-density filter M that absorbs somewhat less incident light, and a blank O that absorbs substantially no incident light. These filters may be changed manually, or they may be changed automatically, for example, by using a filter wheel. Intensity filters also may divert a portion of the light away from the sample without absorption. Examples include beam splitters, which transmit some light along one path and reflect other light along another path, and Pockels cells, which deflect light along different paths through diffraction. Examples also include hot mirrors or windows that transmit light of some wavelengths and absorb light of other wavelengths.

Light next may pass through an emission interference filter 140, which may be housed in an emission filter wheel 142. In apparatus 90, these components are substantially similar to their excitation counterparts, although other mechanisms also could be employed. Emission interference filters block stray excitation light, which may enter the emission path through various mechanisms, including reflection and scattering. If unblocked, such stray excitation light could be detected and misidentified as photoluminescence, decreasing the signal-to-background ratio. Emission interference filters can separate photoluminescence from excitation light because photoluminescence has longer wavelengths than the associated excitation light. Luminescence typically has wavelengths between 200 and 2000 nanometers.

The relative positions of the spectral, intensity, polarization, and other filters presented in this description may be varied without departing from the spirit of the invention. For example, filters used here in only one optical path, such as intensity filters, also may be used in other optical paths. In addition, filters used here in only top or bottom optics, such as polarization filters, may also be used in the other of top or bottom optics or in both top and bottom optics. The optimal positions and combinations of filters for a particular experiment will depend on the assay mode and the composition, among other factors.

Light last passes to a detector, which is used in absorbance, scattering and photolumineseence assays. In apparatus 90, there is one detector 144, which detects light from all modes. A preferred detector is a photomultiplier tube (PMT). Apparatus 90 includes detector slots 145a–d for four detectors, although other numbers of detector slots and detectors also could be provided.

More generally, detectors comprise any mechanism capable of converting energy from detected light into signals that may be processed by the apparatus, and by the processor in particular. Suitable detectors include photomultiplier tubes, photodiodes, avalanche photodiodes, charge-coupled devices (CCDs), and intensified CCDs, among others.

Depending on the detector, light source, and assay mode, such detectors may be used in a variety of detection modes. These detection modes include (1) discrete (e.g., photon-counting) modes, (2) analog (e.g., current-integration) modes, and/or (3) imaging modes, among others, as described in PCT patent application Ser. No. PCT/US99/03678.

B. Chemiluminescence Optical System

FIGS. 5, 6, and 8 show the chemiluminescence optical system of apparatus 50. Because chemiluminescence follows a chemical event rather than the absorption of light, the chemiluminescence optical system does not require a light source or other excitation optical components. Instead, the chemiluminescence optical system requires only selected emission optical components. In apparatus 50, a separate lensless chemiluminescence optical system is employed, which is optimized for maximum sensitivity in the detection of chemiluminescence.

Generally, components of the chemiluminescence optical system perform the same functions and are subject to the same caveats and alternatives as their counterparts in the incident light-based optical system. The chemiluminescence optical system also can be used for other assay modes that do not require illumination, such as electrochemiluminescence.

The chemiluminescence optical path begins with a chemiluminescent composition 120 held in a sample holder 126. The composition and sample holder are analogous to those used in photoluminescence assays; however, analysis of the composition involves measuring the intensity of light generated by a chemiluminescence reaction within the composition rather than by light-induced photoluminescence. A familiar example of chemiluminescence is the glow of the firefly.

Chemiluminescence light typically is transmitted from the composition in all directions, although most will be absorbed or reflected by the walls of the sample holder. A portion of the light transmitted through the top of the well is collected using a chemiluminescence head 150, as shown in FIG. 5, and will follow a chemiluminescence optical pathway to a detector. The direction of light transmission through the chemiluminescence optical system is indicated by arrows.

The chemiluminescence head includes a nonconfocal mechanism for transmitting light from a sensed volume within the composition. Detecting from a sensed volume reduces contributions to the chemiluminescence signal resulting from "cross talk," which is pickup from neighboring wells. The nonconfocal mechanism includes a chemiluminescence baffle 152, which includes rugosities 153 that absorb or reflect light from other wells. The nonconfocal mechanism also includes a chemiluminescence aperture 154 that further confines detection to a sensed volume.

Light next passes through a chemiluminescence fiber optic cable 156, which may be replaced by any suitable mechanism for directing light from the composition toward the detector. Fiber optic cable 156 is analogous to excitation and emission fiber optic cables 1110a,b and 134a,b in the photoluminescence optical system. Fiber optic cable 156 may include a transparent, open-ended lumen that may be filled with fluid. This lumen would allow the fiber optic to be used both to transmit luminescence from a microplate well and to dispense fluids into the microplate well. The effect of such a lumen on the optical properties of the fiber optic could be minimized by employing transparent fluids having optical indices matched to the optical index of the fiber optic.

Light next passes through one or more chemiluminescence intensity filters, which generally comprise any mechanism for reducing the intensity of light. In apparatus 50, intensity is altered by chemiluminescence neutral density filters 158. Light also may pass through other filters, if desired.

Light last passes to a detector, which converts light into signals that may be processed by the apparatus. In apparatus 50, there is one chemiluminescence detector 160. This detector may be selected to optimize detection of blue/green light, which is the type most often produced in chemiluminescence. A preferred detection is a photomultiplier tube, selected for high quantum efficiency and low dark count at chemiluminescence wavelengths (400–500 nanometers).

C. Housing

Figure 9:
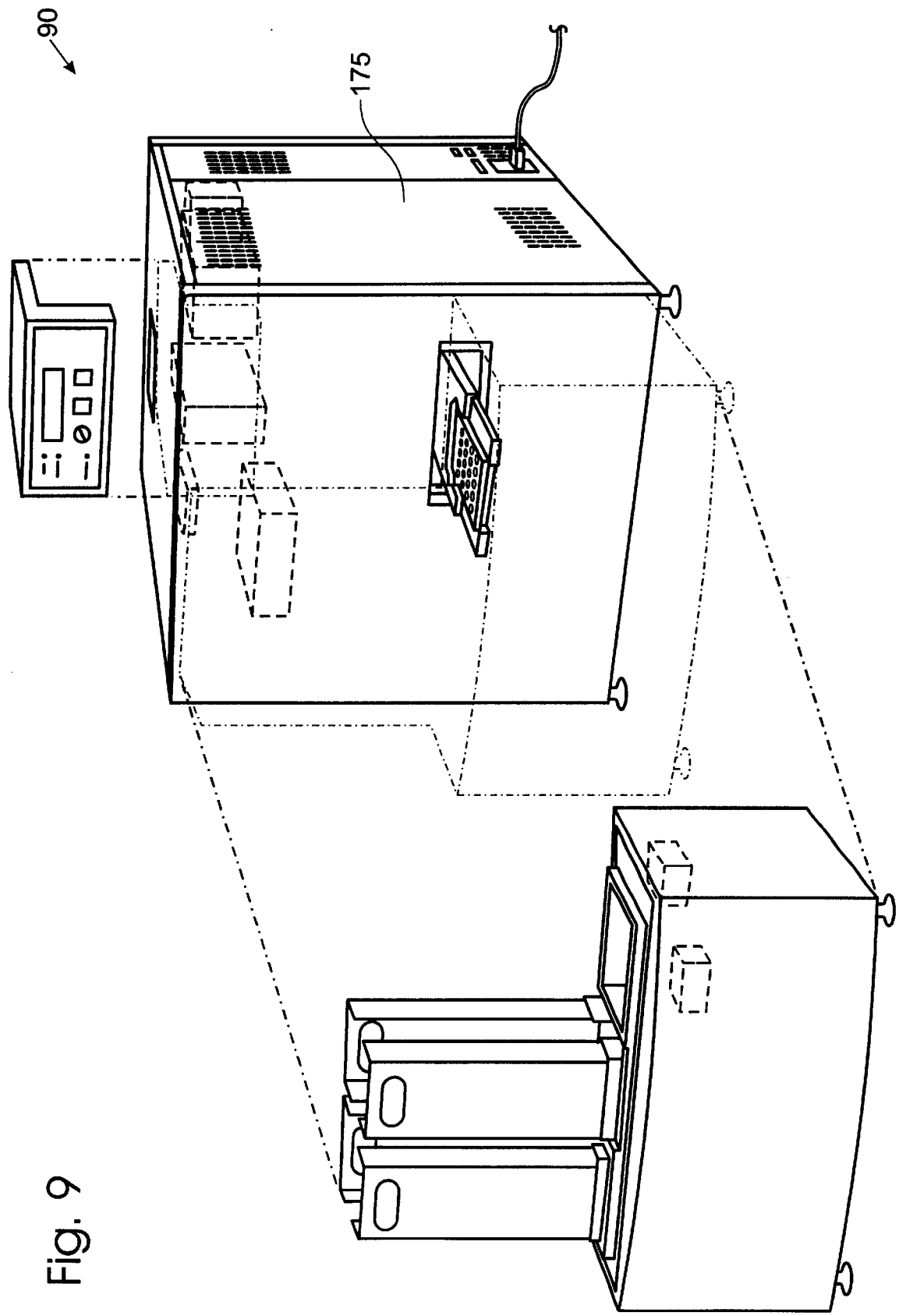
FIG. 9 is a partially exploded perspective view of a housing for the apparatus of FIG. 5.

FIG. 9 shows a housing 175 and other accessories for the apparatus of FIGS. 5–8. Housing 175 substantially encloses the apparatus, forming (together with light source slots 103a–d) two protective layers around the continuous high color temperature xenon arc lamp. Housing 175 permits automated sample loading and switching among light sources and detectors, further protecting the operator from the xenon arc lamp and other components of the system. Additional details of an apparatus suitable for implementing features of the invention are shown in U.S. patent application Ser. No. 09/160,533, which is incorporated herein by reference.

D. Freuency-domain Detection System

Figure 10:
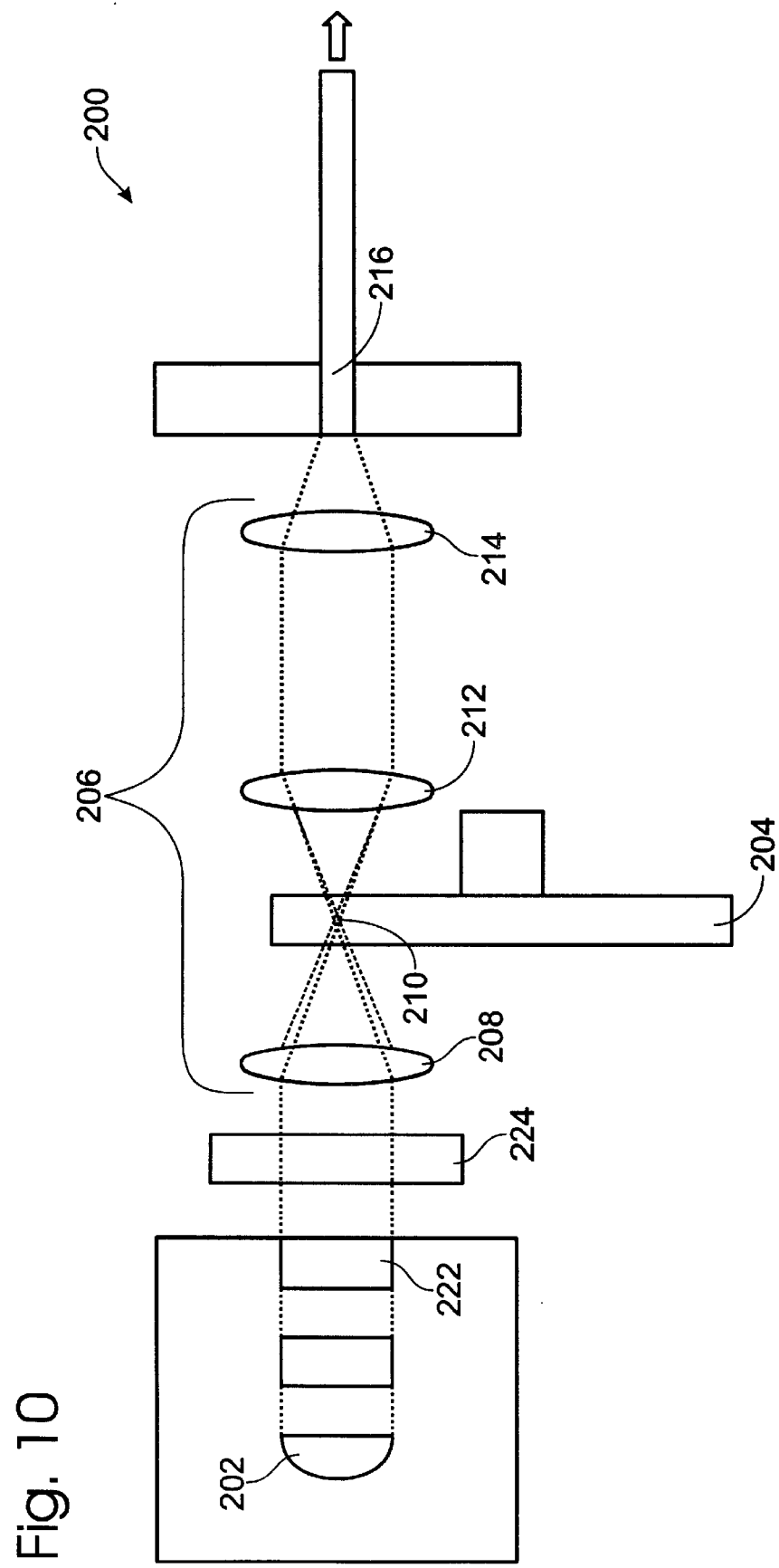
FIG. 10 shows a portion of an apparatus for producing time-modulated excitation light in accordance with the invention.

FIG. 10 shows a portion 200 of an apparatus for producing time-modulated excitation light in accordance with the invention. Portion 200 includes a light source 202, an optical modulator 204, and focusing optics 206. Remaining portions of the apparatus may include additional light sources, optical modulators, focussing optics, optical relay structures, examination (or measurement) sites, and detectors; these portions may be configured as described above for apparatus 90 and below for apparatus 260.

Light source 202 generally includes any light source configured to produce light for optical spectroscopy. The light source may be continuous, pulsed, or modulated, among others. Suitable light sources include arc lamps, incandescent lamps, fluorescent lamps, light-emitting diodes, electroluminescent devices, lasers, and laser diodes, among others.

Time-resolved luminescence assays generally use time-modulated excitation light. Some light sources inherently produce time-modulated light, so that they may be used without an optical modulator for time-resolved assays; examples include flash lamps and pulsed lasers. However, these sources have a number of shortcomings, including typically low repetition rates, meaning that they are off most of the time. Measurement times in time-resolved luminescence assays employing these sources can exceed 1 second, particularly if high sensitivity is required. Measurement times can be even longer if more information is extracted from the time decay signal, for example, by using multiple integration windows and/or more complex signal processing algorithms and strategies. Conventional flash lamps have pulse widths of about 1 microsecond, and so can only be used with difficulty to measure lifetimes less than about 1 microsecond. Pulsed nitrogen lasers are expensive and have a limited spectral output.

Other light sources do not inherently produce time-modulated light, so that they generally must be used with an extrinsic optical modulator for time-resolved assays; examples include continuous arc lamps and incandescent lamps. Continuous light sources, especially continuous xenon arc light sources, typically provide a higher signal-to-noise ratio in a given measurement time than flash lamps or at least some pulsed lasers. A preferred continuous light source is a continuous high color temperature xenon arc lamp. The xenon lamp has a broad spectrum output, which may be filtered as described above to generate substantially monochromatic light. A continuous xenon arc lamp produces a 10–100 fold higher photon flux than a xenon flash lamp, even with short (e.g., millisecond) integration times. (Xenon flash lamps have a higher peak photon flux than continuous arc lamps; however, their low repetition rate results in a lower average photon flux delivered to the sample.) Because the signal-to-noise ratio is proportional to the square root of the number of photons delivered, the signal-to-noise ratio obtained with continuous arc lamps is 3–10 times higher than the signal-to-noise ratio obtained with flash lamps. Measurement times using an arc source can be as low as 100 milliseconds or lower. These concepts are described more fully below in Section 3.

Optical modulator 204 generally includes any device configured to modulate incident light. The optical modulator may be acousto-optical, electro-optical, or mechanical, among others. Suitable modulators include acousto-optical modulators, Pockels cells, Kerr cells, liquid crystal devices (LCDs), chopper wheels, tuning fork choppers, and rotating mirrors, among others. Mechanical modulators may be termed "choppers," and include chopper wheels, tuning fork choppers, and rotating mirrors.

Some optical modulators may be configured to produce multi-frequency modulation, with up to 100% modulation and no attenuation in the on state; examples include choppers. The net attenuation of a mechanical modulator is determined by the fraction of time that its aperture is clear. The net attenuation of a chopper outputting light having a square-wave modulation varying abruptly between zero and maximum intensity levels is 50%. Mechanical modulators, such as chopping wheels and tuning forks, may have small clear apertures (several millimeters), permitting them to operate at high frequencies. Indeed, conventional mechanical choppers may be used to obtain chopping speeds up to about 10–20 kilohertz or more, allowing accurate lifetime measurements down to about 5–10 microseconds ($\tau_{min}$=tan(30°)/(2πf)) or less. Special mechanical choppers, such as dual rotating wheel choppers, may be used to obtain even higher frequencies, up to about 100 kilohertz or more. Alternatively, mechanical choppers may be used at lower chopping speeds, especially for measurements of longer decay times.

A chopper also may be used in steady-state spectroscopic assays, including steady-state intensity and polarization assays, for synchronous detection in conjunction with a lock-in amplifier to reduce background components of the signal. Such background may include ac or dc ambient light and white noise or 60-cycle noise inherent in electronic circuitry.

Focusing optics 206 generally includes any mechanism configured to arrange at least a portion of the light (dashed lines) produced by light source 202 so that it may pass through the modulator for modulation. The focusing optics may include one or more lenses. In portion 200, the focusing optics includes three lenses. A first lens 208 collects substantially collimated light from the light source and focuses it so that it narrows to a waist 210 at a focal point in a focal plane of the lens and then diverges. A second lens 212 collects and collimates the diverging light. A third lens 214 focuses the collimated light from the second lens so that it impinges on a fiber optic cable 216 or other optical component for relay to an examination or measurement site. In other embodiments, the focusing optics may include other lenses and/or optical components, as required or preferred. For instance, if the chopper is relocated adjacent the fiber optic cable, i.e. to the right in FIG. 10, lenses 212 and 214 may be eliminated. In this case, the chopper would be positioned adjacent the focal point, which is positioned at the input of the fiber optic cable. As a result of not being located at the focal point, however, it may be necessary to provide larger apertures on the chopper.

The optical modulator generally may be positioned in any location along the light path in which it may modulate the beam. In portion 200, optical modulator 204 is positioned at or near focal point 210 of focusing optics 206. Light passing through the focal point is narrower, so that the optical modulator can be smaller and still occlude the beam to effect modulation. A smaller modulator uses less space, so that the associated optical device may be smaller. A smaller modulator also may be faster, cheaper, and/or less prone to vibration. In some embodiments, it may be preferable to use a larger modulator, in which case the focusing optics may be omitted.

Portion 200 may include other components, such as a Uv hot mirror 222 and/or one or more filters 224, such as spectral, intensity, and/or polarization filters.

Figure 11:
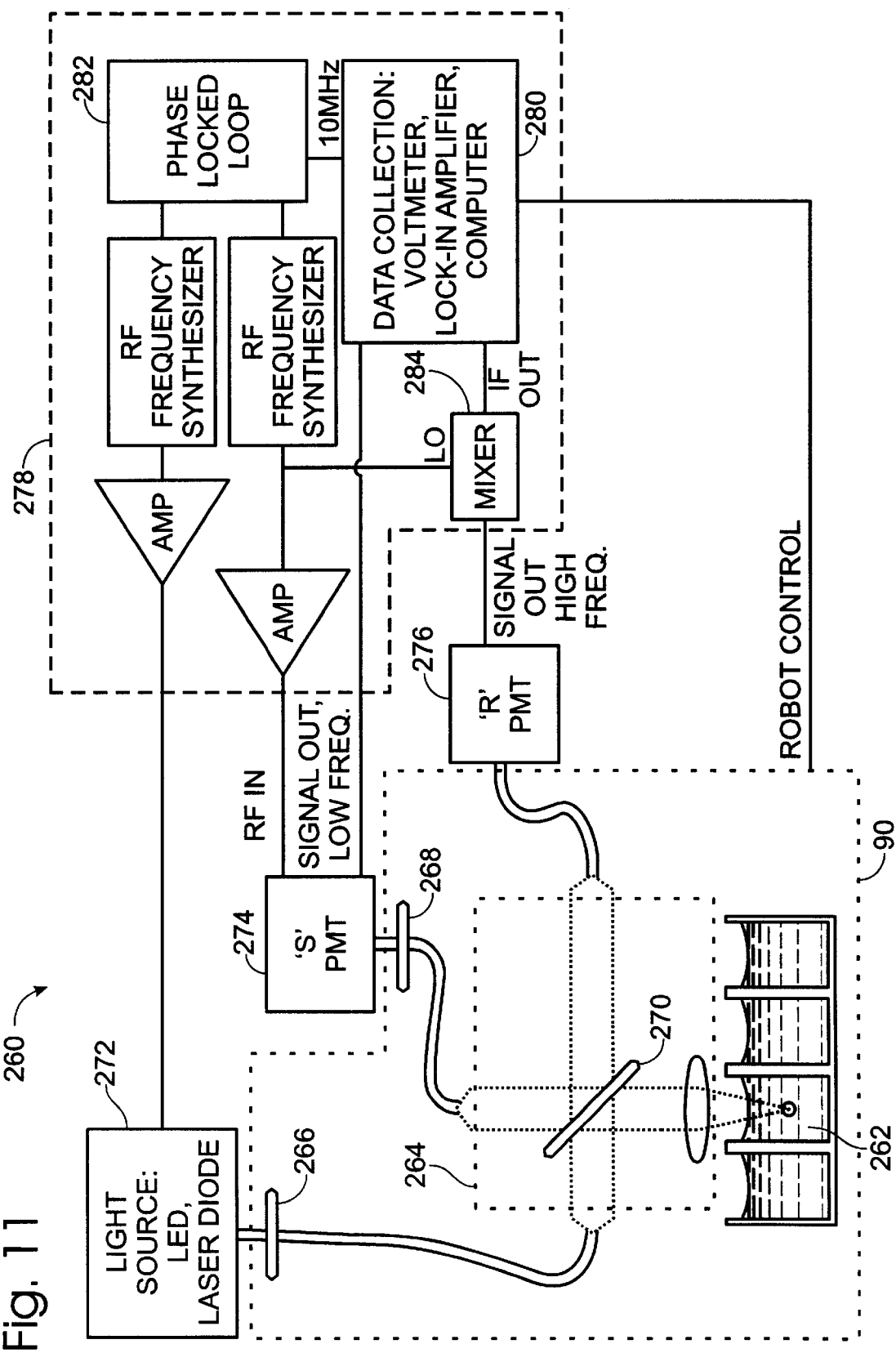
FIG. 11 is a schematic view of an apparatus for detecting time-modulated light in accordance with the invention.

FIG. 11 shows an apparatus 260 for detecting light emitted by an analyte in a composition 262, where the detection and/or processing may be performed in the frequency-domain. Apparatus 260 includes substantial portions of apparatus 90, including its fiber-optic-coupled optics head 264, excitation 266 and emission 268 filters, dichroic beam splitter 270, and mechanisms for sample positioning and focus control. However, apparatus 260 also may include alternative light sources 272, sample ('S') detectors 274, reference ('R') detectors 276, and detection electronics 278. In FIG. 11, alternative components 272–278 are shown outside apparatus 90, but they readily may be included inside housing 250 of apparatus 90, if desired.

Apparatus 260 may provide incident light in various ways, as described above. For example, analytes absorbing blue light may be excited using a NICHIA-brand bright-blue LED (Model Number NSPB500; Mountville, Pa.). This LED produces broad-spectrum excitation light, so excitation filter 266 typically may be selected to block the red edge of the spectrum. If analytes are excited using a laser diode, an excitation filter is not necessary.

Apparatus 260 may detect emitted light and convert it to a signal in various ways. This demodulation/deconvolution may be internal to the photodetector, or it may be performed with external electronics or software. For example, emitted light can be detected using sample detector 274, which may be an ISS-brand gain-modulated PMT (Champaign, Ill.). High-frequency emitted light can be frequency down-converted to a low-frequency signal using a technique called heterodyning. The phase and modulation of the low-frequency signal can be determined using a lock-in amplifier 280, such as a STANFORD RESEARCH SYSTEMS brand lock-in amplifier (Model Number SR830; Sunnyvale, Calif.). Lock-in amplifier 280 is phase locked using a phase-locked loop 282 to a modulation frequency of light source 272, such as the fundamental frequency or a harmonic thereof. To correct for drift in the light source, the output of light source 272 may be monitored using reference detector 276, which may be a HAMAMATSU-brand PMT (Model Number H6780; Bridgewater, N.J.). If reference PMT 276 can respond to high-frequency signals, the heterodyning step can be performed using an external mixer 284. The phase and modulation of reference PMT 276 also may be captured by lock-in amplifier 280 and used to normalize the signal from sample PMT 274.

A computer or processor controls the apparatus, including the external components. The computer also directs sample handling and data collection. Generally, phase and modulation data are collected at one or more frequencies appropriate for the lifetime of the analyte. In some cases, phase and modulation may be measured at one or a few frequencies and processed by the computer or processor to help reduce detected background.

The invention also may employ other apparatus or optical devices having yet other combinations of components. Such apparatus and devices may have a high color temperature light source and/or be capable of detecting light substantially exclusively from a sensed volume.

In summary, incorporating a continuous arc lamp with a UV hot mirror, fluorescence interference filter, mechanical chopper, and appropriate lenses into an analyzer such as a high-throughput analyzer provides new apparatus and methods for measuring signals from long-lived reporter groups with reduced measurement times, increased signal-to-noise ratios, and improved rejection of background signals and quality control.

2. Luminescence Assays

Apparatus 50, 90, and 260 may be used to conduct a variety of steady-state and time-resolved luminescence assays. Steady-state assays measure luminescence under constant illumination, using the continuous light source. Time-resolved polarization assays measure luminescence as a function of time, using either the continuous light source, with its intensity appropriately modulated, or the time-varying light source.

A. Intensity Assays

Intensity assays may be conducted by monitoring the intensity of the luminescence emitted by the composition.

B. Polarization Assays

Polarization assays may be conducted as follows. Excitation light from the continuous light source is directed through an excitation filter, low-luminescence fiber optic cable, and excitation polarization filter. Excitation light then is directed to a beamsplitter, which reflects most of the light onto a composition and transmits a little of the light into a light monitor. Emitted light from the composition is directed back through the beamsplitter and then is directed through another low-luminescence fiber optic cable, an emission filter, and a polarization filter (in either the S or P orientation) before detection by a photomultiplier tube or other detector. Two measurements are performed for each composition, one with excitation and emission polarizers aligned and one with excitation and emission polarizers crossed. Either polarizer may be static or dynamic, and either polarizer may be set in the S or P orientation, although typically the excitation polarizer is set in the S orientation.

Steady-state polarization assays also may be conducted by constantly polarizing and transmitting high color temperature light to an examination site as successive samples are automatically, serially aligned in an optical path intersecting the examination site, and detecting polarized light emitted from each sample.

C. Time-Resolved Assays

The invention provides apparatus and methods for performing time-resolved luminescence assays.

One aspect of the invention provides a system for measuring the temporal response properties of a luminescent sample. In this aspect, a light source outputs a light beam having relatively constant intensity, and the outputted light beam is modulated to create modulated incident light that may be used to excite luminescence from a luminescent sample. The modulated light ranges in intensity from a maximum that is substantially equal to the relatively constant intensity of the light beam originally outputted from the light source to a minimum that is less than one-quarter of the maximum intensity. Suitable optical modulators for producing such modulation ranges include choppers, which may be configured to produce light having a minimum intensity substantially equal to zero.

Another aspect of the invention provides a time-resolved spectroscopic assay. In this aspect, a light source having a broad spectrum output is used, and a substantially monochromatic component of the output is extracted and passed through a chopper to create periodically modulated incident light.

In each aspect, the modulated light is used to illuminate a sample, so that a luminescence output is generated, and the phase and/or modulation of the luminescence output is determined. In turn, the phase and/or modulation may be used to compute a temporal response characteristic of the sample, including one or more luminescence lifetimes and/or one or more rotational correlation times. Mechanisms for computing lifetimes and/or correlation times are described above and in PCT patent application Ser. No. PCT/US99/01656, and Joseph R. Lakowicz, *Principles of Fluorescence Spectroscopy* (1983), both of which are incorporated herein by reference.

In some aspects, the apparatus may use high duty cycle, high frequency-content excitation (roughly a square or rectangular wave) to detect or measure luminescence lifetimes and/or rotational correlation times, instead of using pulsed or sine wave excitation. High duty cycle, high frequency content excitation may be produced by a chopper. The apparatus also may use a continuous arc lamp, reducing integration time or increasing signal to noise ratio.

Generally, the relationship between time-domain data and frequency-domain data is given by a Fourier transform. If the time-domain data are periodic, they may be expressed using the simpler Fourier series, which decomposes the data in terms of sines and cosines. Specifically, the Fourier series decomposition of a piecewise regular function f(t), defined on an interval $T_0 \leq t \leq T_0+T$, may be expressed as follows:

$$f(t) = \frac{a_0}{2} + \sum_{n=1}^{\infty} [a_n \cos(n\omega t) + b_n \sin(n\omega t)] \quad (7a)$$

$$\begin{cases} a_n = \frac{\omega}{\pi} \int_{T_0}^{T_0+T} f(t)\cos(n\omega t)\,dt \\ b_n = \frac{\omega}{\pi} \int_{T_0}^{T_0+T} f(t)\sin(n\omega t)\,dt \end{cases} \quad (7b)$$

Here, c and T>0 are constants.

The excitation light produced by a mechanical chopper generally will approximate a square or rectangular wave, with relatively sharp transitions between light and dark, although other illumination patterns are possible. A square-wave having a period $T=2\pi/\omega_s$ produced by a chopper having a 50% duty cycle may be written as follows:

$$f_{EX}(t) = \begin{cases} H & 0 \leq t \leq \pi/\omega_s \\ 0 & \pi/\omega_s < t \leq 2\pi/\omega_s \end{cases} \quad (8)$$

This function is piecewise regular, and may be re-expressed using the Fourier series as a sum of sines, where each sine is associated with a different frequency.

$$f_{EX}(t) = \frac{H}{2} + \sum_{n=1,3,5,...} \frac{2H}{n\pi} \sin(n\omega_s t) \qquad (9)$$

Equation 9 shows that the square wave may be decomposed using Fourier components having angular frequencies $\omega_s$, $3\omega_s$, $5\omega_s$, $7\omega_s$, .... The amplitudes of these components are inversely proportional to frequency, so that the amplitudes decrease as the frequencies increase. Here, $\omega_s$ is the fundamental frequency, $\omega_s$, $3\omega_s$, $5\omega_s$ and $7\omega_s$, are the first, third, fifth, and seventh harmonics, and $3\omega_s$, $5\omega_s$ and $7\omega_s$, are the second, fourth, and sixth overtones.

Fourier analysis also may be applied to other excitation wave forms, including rounded or smeared square waves. Generally, the mixture of harmonics may be varied by varying the duty cycle of the wave form. For example, if the duty cycle is decreased, corresponding to decreasing the on (f(t)=H) time and increasing the off (f(t)=0) time, the amplitude of the higher harmonics will increase. Consequently, for a fixed chopper frequency, the modulation frequencies can be varied by varying the duty cycle.

Luminescence assays used to calculate can be a decay time or a temporal response characteristic of a sample, such as luminescence lifetimes and/or a rotational correlation times. In frequency-domain measurements, for rectangular waves, the on time may be larger, smaller, or the same as the decay time. In contrast, in time-resolved measurements, the on time should be less than the decay time, typically several times less.

Periodic excitation will produce periodic luminescence, which also can be characterized using Fourier series. As described above, a signal processing system can be used to track the phase and/or modulation of the luminescence relative to the phase and/or modulation of the excitation light. This analysis may be performed for each frequency present in the excitation and emission signals, although it becomes progressively more difficult as frequency increases because the associated amplitudes decrease. For this reason, signal detection and/or data analysis may focus on such lower frequency terms, particularly the fundamental.

Higher-frequency components of the output signal can be used with appropriate detection systems to extend the effective frequency of the mechanical chopper 3-fold, 5-fold, 7-fold, or more, as long as a sufficient signal-to-noise ratio exists. This extends the minimum lifetime that can be analyzed to proportionately lower values, without requiring an increase in the fundamental frequency of the chopper.

Decay times corresponding to luminescence lifetimes and/or rotational correlation times, among others, can be determined by fitting these phase and modulation data to an appropriate model. For example, if there is a single luminescence lifetime, the data may be fit to Equations 5 and/or 6, as presented above. If there is more than one luminescence lifetime, or if there is molecular reorientation during a polarization experiment, then a more complicated model may be required, such as a two-lifetime and/or two-rotational-correlation-time model.

More complex models may use phase and/or modulation information at two or more frequencies. Multi-frequency information can be measured using a one or more mechanical choppers in various ways.

In systems containing a single chopper, multi-frequency information can be obtained by changing the frequency of the chopper or by using different harmonics of the modulated light. The frequency of the chopper can be changed during analysis of each sample, or it may be changed after analysis of a series of samples for reanalysis of the series of samples at a second frequency. Unfortunately, the frequency of some choppers, such as resonant tuning fork choppers, may be difficult to change. The different harmonics of the modulated light may be used through Fourier analysis, or by changing frequency on a lock-in amplifier or other frequency-dependent detection system. For instance, one or more filters may be connected to the output of the detector to extract selected harmonic frequencies from the detector. Typically, filters, such as a Bessel filter would be chosen to impart the least perturbation on the passed frequency components.

In systems containing multiple choppers, multi-frequency information can be obtained by switching combinations of choppers and/or light paths. Choppers may be switched by moving choppers in and out of the light path, for example, by using a solenoid. Light paths may be switched optically, or otherwise by routing light first through one chopper and then through a second chopper.

If the optical modulator has sufficient frequency and UV response, phase or phase and modulation techniques can be used to measure signals from long-lived luminophores, such as metal-ligand complexes containing ruthenium, osmium, etc. ($\tau$=50 ns–5 $\mu$s), and lanthanide chelates containing europium, terbium, etc. ($\tau$=50 $\mu$s–5 ms). In addition, the intensity of light from long-lived luminophores can be measured in the presence of relative large amounts (100×) of background from typically shorter-lifetime luminophores associated with the sample container, assay components, and compounds being screened. Generally, time-resolved luminescence assays can be performed in combination with methods for reducing or eliminating background, identifying quenching, and more rapidly collecting signals. Suitable methods are described in U.S. Provisional patent application Ser. No. 60/094,306 and PCT patent application Ser. Nos. PCT/US99/01656 and PCT/US99/03678, each of which is incorporated herein by reference, as well as in other patent applications and books listed above under Cross-References.

D. Miscellaneous Assays

Additional luminescence assays, including fluorescence resonance energy transfer (FRET), total internal reflection fluorescence (TIR), fluorescence correlation spectroscopy (FCS), and fluorescence recovery after photobleaching (FRAP), as well as their phosphorescence analogs, may be conducted using procedures outlined in the patent applications and books cross-referenced above and/or generally known to persons of ordinary skill in the art.

3. Enhancement of Signal

Achieving good signal-to-noise and signal-to-background ratios from dilute samples is critical in absorbance, scattering, luminescence polarization and other assays supported by the apparatus. For example, in a binding assay, it often is desirable to be able to probe binding involving molecules with dissociation constants in the sub-nanomolar range. This is facilitated by being able to achieve acceptable signal-to-noise and signal-to-background ratios from compositions with luminophore concentrations in the sub-nanomolar range. The methods of signal-to-noise and signal-to-background enhancement discussed below permit the apparatus to achieve the required sensitivity with such dilute samples, thereby minimizing reagent cost, which otherwise can be considerable.

Sensitivity also is enhanced by reducing the contribution of noise to the measurements. In luminescence polarization assays, various factors contribute to noise, including (1) background noise and (2) intensity noise. Background noise refers to contributions to the signal from luminescent species other than the luminescent species of interest, including luminescent species in the apparatus and sample holder. Intensity noise refers to fluctuations in light intensity, including those arising from photon noise.

Background noise may be reduced by reducing autoluminescence from the apparatus and sample holder. For example, the apparatus may use low luminescence components, such as fused silica fiber optic cables. Similarly, the sample holder may be constructed using low luminescence materials, such as black polystyrene and/or carbon black. Suitable microplate compositions are described in PCT patent application Ser. No. PCTIUS99/08410, which is incorporated herein by reference.

Background noise also may be reduced by reducing detection of luminescence from components of the sample that are bound to the sample holder and immobilized, which otherwise would lead to spuriously high luminescence polarization. For example, the walls of the sample holder may be constructed or treated to reduce binding. Alternatively, in an apparatus capable of detecting light transmitted substantially exclusively from a sensed volume, the sensed volume may be positioned near the center of the composition, away from the walls of the sample holder.

Intensity noise may be reduced by correcting for fluctuations in light source intensity, among others. Light source fluctuations arise due to fluctuations in power from the power supply and drift in the position of the arc in arc lamps, among others. Light source fluctuations will lead to luminescence fluctuations, because the amount of emitted light in luminescence or absorbance is proportional to the amount of excitation light. Luminescence fluctuations are especially important in polarization assays, because such assays involve comparing the magnitude of successively measured signals. Light source fluctuations may be reduced by choosing a stable light source and by rescaling the emitted light signal using information obtained from a light source monitor, as described above.

Intensity noise also may be reduced by increasing the number of photons (amount of light) detected, which reduces photon noise. Photon (or shot) noise arises due to the statistical nature of light and may be described by the same statistical law used to describe radiation decay. In particular, if N photons are detected during a given time interval, the standard deviation associated with that number due to photon noise will be $\sqrt{N}$. The relative significance of photon noise decreases as the number of detected photons increases, because the ratio of the standard deviation in the signal to the signal goes as $\sqrt{N}/N=1/\sqrt{N}$. Although there may be many sources of intensity noise, the limit set by photon noise can never be overcome; however, the significance of photon noise can be reduced by increasing the number of photons collected by the detector. The number of photons collected may be increased by increasing the intensity of the light source, the efficiency of the detector, and/or the throughput of components of the optical relay structure, such as the beamsplitter, among others.

Photon noise creates noise in polarization assays. To a very good approximation, the noise in the polarization is proportional to the noise in the intensities from which the polarization is calculated and corresponds to seven miP standard deviation in polarization for every one percent standard deviation in intensity. This relationship essentially is independent of the degree of polarization. Because of photon noise, the requirement for rapid high-throughput screening measurements in the optically restrictive microplate format puts a premium on simply collecting enough light. For additional information, see PCT patent application Ser. No. PCT/US98/23095, which is incorporated herein by reference.

Most well-developed polarization assays have maximum polarization changes of between 100 mP and 200 mP, so acceptable standard deviations in the polarization should be no greater than about 5 mP to 10 mP. This requires detection of at least 10,000 photons per intensity measurement to reduce intensity noise to about 1%. The inefficiency of polarization optical systems increases the problem. The number of photons collected is proportional to both the concentration and the detection time, leading to trade-offs between probe concentration and screening throughput. High concentrations of reagents not only are expensive, but also produce insensitive binding assays if they exceed the dissociation constant of the binding reaction.

The various absorbance and scattering assays described below can also be used in conjunction with luminescence assays to improve accuracy. For example, a sample that has significant absorbance or scattering will have reduced luminescence signal. By monitoring absorbance or scattering, it is possible to correct for changes in luminescence that are a result of absorbance or scattering variations.

4. Absorbance Assays

Figure 12:
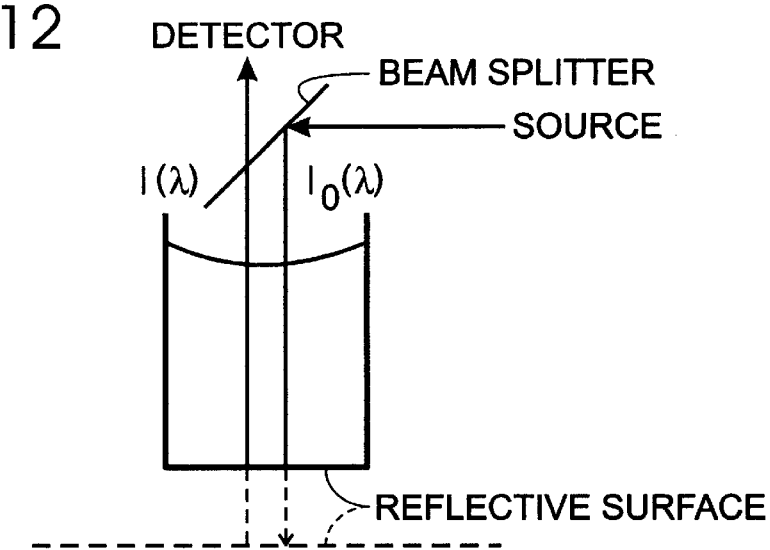
FIG. 12 is a schematic view of an absorbance experiment conducted in accordance with the invention.

FIG. 12 shows a schematic view of an absorbance assay performed in accordance with the invention. Incident light from a light source is reflected onto the sample by a beam splitter. The light passes a first time through the sample, bounces off a reflective surface at the far side of the sample, and passes back a second time through the sample. Transmitted light emerges from the sample and passes through the beam splitter to a detector. The optical paths between the light source and sample, and the sample and light detector, may lie along different optical axes, or they may lie along the same optical axis, as when a fiber optic bundle having parallel excitation and emission fibers is employed.

In a preferred embodiment, the absorbance assay is performed using a high-throughput analyzer, such as described above and disclosed in the patent applications cross-referenced above. In this embodiment, a 50/50 beam splitter is employed, one of the two spectral filters normally used for luminescence is removed, and the other of the two spectral filters is selected to match an absorbance band of interest of the sample. In addition, the focal plane of the confocal optics is adjusted so that the instrument focuses on the far side of the sample container. It should be noted that than attenuator may be necessary between the sample and the detector to reduce the light level to a range useable by the detector. Because luminescence levels are typically very low compared to incident light levels and reflected light levels, the majority of the light reaching the detector will consist of reflected light that has passed twice through the sample in the described arrangement. Where reflected light levels are lower, it is also possible to filter out luminescence light or other light sources so that primarily reflected light reaches the detector. A reference sample well containing a blank, i.e. without the analyte of interest, may be used to correct for absorbance by the solution, optics, or other non-sample components of the assay. In a preliminary experiment in a 96-well microplate, absorbance over a range of 1.2 ODs was measured with about 0.1 OD resolution and acceptable linearity.

The reflective surface may include the sample wall or an additional surface. For example, the reflective surface may include a partially reflective sample wall, such as the bottom of a clear microplate, the interior surface of a white microplate, or a totally reflective sample wall, such as a sample wall with a silvered surface. Alternatively, the reflective surface may include an additional surface, such as a mirror placed inside or outside the sample container, as shown by the dashed lines in FIG. 12. Reflection from the reflective surface may occur by a variety of mechanisms, including total internal reflection.

Figure 13:
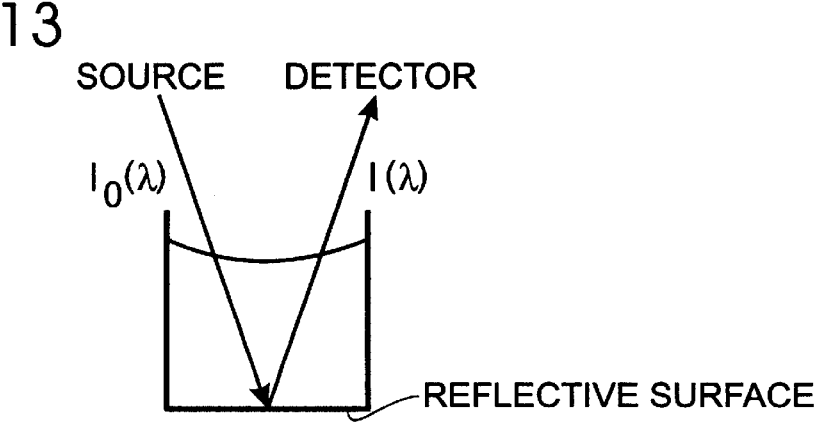
FIG. 13 is a schematic view of an alternative absorbance experiment conducted in accordance with the invention.

FIG. 13 shows a schematic view of an alternative absorbance assay performed in accordance with the invention. Light enters and exits through an open side of the sample container, and may be reflected by the sample wall or by a mirror inside or outside the sample wall. This alternative absorbance assay does not involve a beam splitter, and may not involve passage of light through any wall of the sample container. This alternative absorbance assay does provide an extended path length, which arises because light travels through the sample at an angle, further increasing absorbance. Path length similarly may be extended in other embodiments, including embodiments incorporating beam splitters.

Figure 14:
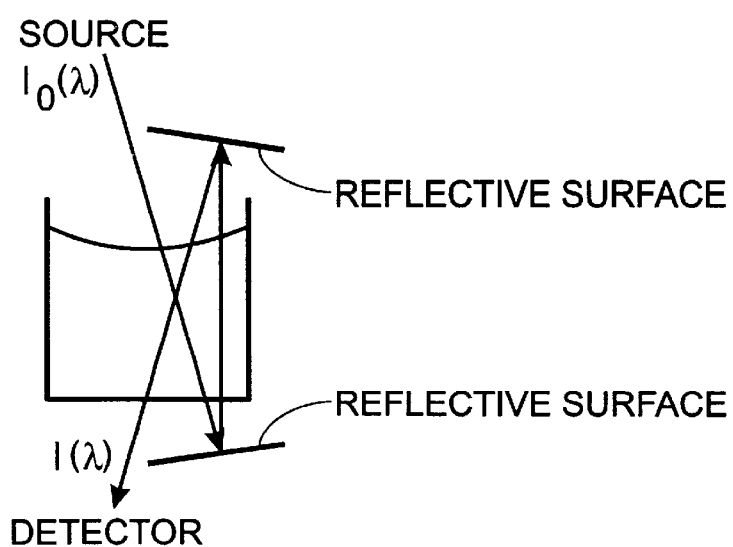
FIG. 14 is a schematic view of another alternative absorbance experiment conducted in accordance with the invention.

FIG. 14 shows that light may be directed through the sample more than twice.

The absorbance assay minimizes the influence of the sample meniscus on assay results. In particular, refractive effects due to the meniscus are minimized because they are reversed on the return trip after the light reflects off the far side of the sample container. Additional corrections for effects such as meniscus variations may be made by referencing a measurement at the wavelength at which absorbance is to be determined by an absorbance-mode measurement in the same sample container at one or more other wavelengths where there is no absorption, essentially a ratiometric strategy.

As mentioned above, absorbance assays also may be used to improve fluorescence and other luminescence assays. For example, absorbance measurements can be paired with luminescence measurements to detect "color quenching" of fluorescence assays. "Color quenching" is a term used to describe the absorbance of excitation or luminescence emission light in samples that happen to have significant extinction coefficients at those wavelengths. The result is a decrease in the measured luminescence intensity, which may significantly interfere with assay interpretation. The result of an absorbance measurement can be used to correct the measured luminescence back to the value that would have been obtained in the absence of absorbance.

A separate, simultaneous or subsequent absorbance measurement made at the excitation and/or emission wavelength can identify the existence of color quenching and may provide a means of correcting the luminescence signal for this interference. If a dichroic beamsplitter is used for the luminescence measurements, the beamsplitter will significantly attenuate the signal used in the absorbance measurement. It is preferable not to have to switch to a wavelength-insensitive (e.g., 50/50) beamsplitter when making the absorbance measurement after the luminescence measurement. The intensity of the reflected light used in the absorbance measurement generally will be much higher than the intensity of luminescence and may be attenuated before reaching the detector; the attenuation caused by the dichroic beam splitter likely can serve this function.

Figure 15:
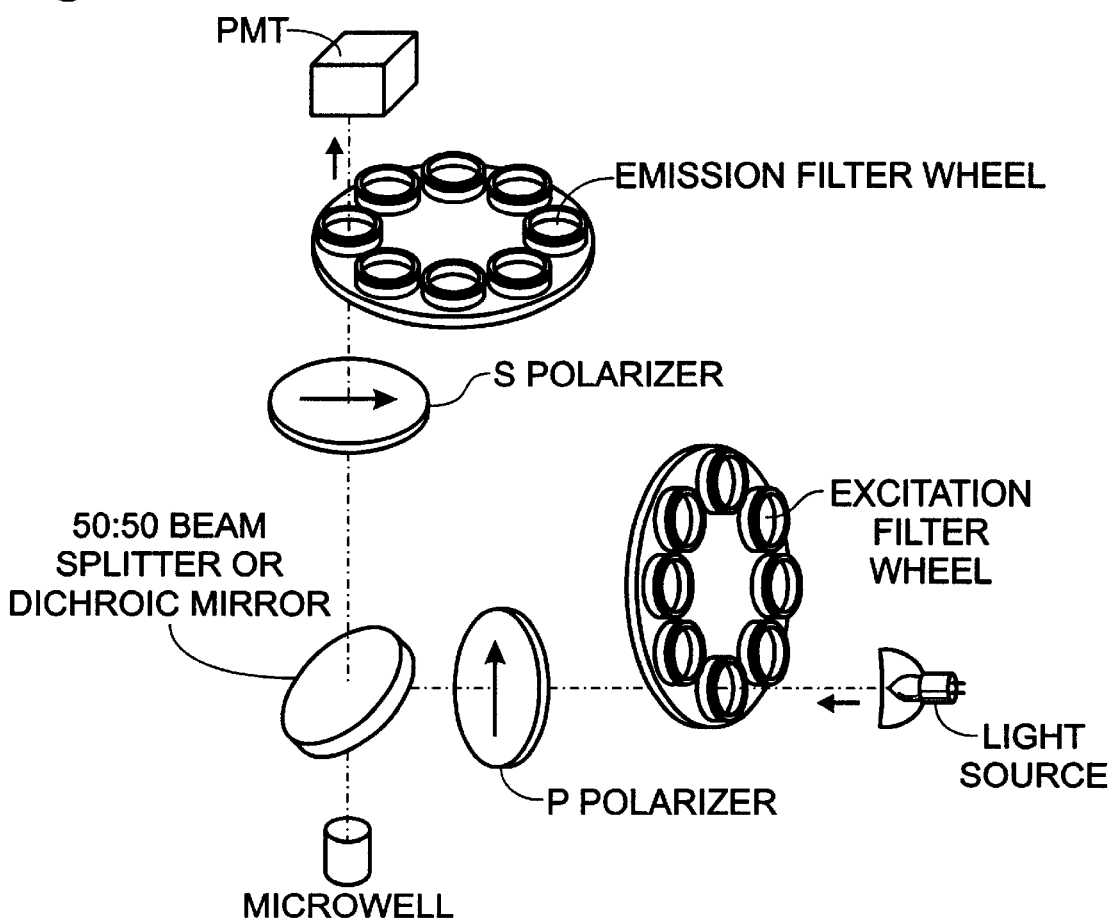
FIG. 15 is a schematic view of an apparatus for conducting an absorbance experiment, in which the apparatus is constructed in accordance with the invention.

FIG. 15 shows an apparatus for conducting an absorbance measurement constructed in accordance with the invention. The apparatus employs the reflective absorbance configured as described above. The apparatus can give a simultaneous indication of reflectance, scattering, and absorbance of a sample in a microplate well or other sample container in a top down (i.e., non-transmissive) configuration. This method can be used with white, black, or clear bottom microplates. The sensitivity of the method can be enhanced with the insertion of crossed polarizers. Reflective absorbance sensitivity is further optimized by selection of the appropriate focal height within the sample well.

The response linearity of this method can be improved by determining the amount of "excess intensity" (which includes background light and reflected light) and subtracting it from the raw intensities prior to calculating the absorbance. Mathematically, the raw intensity $I_{Raw}$ was assumed to include light that passed through the sample $I_{Sample}$ and instrument background $I_{Bkg}$:

$$I_{Raw} = I_{Sample} + I_{Bkg} \tag{10}$$

The raw intensities then were curve-fit to a pseudo-Beer's law model, where $I_{Bkg}$ and K were selected using a nonlinear least-squares fitting method:

$$A = -\log_{10}\left[\frac{I_{Raw} - I_{Bkg}}{I_{RawBuffer} - I_{Bkg}}\right] = K \times C_{Sample} \tag{11}$$

This simple linearization scheme can be used to produce reasonably linear responses over >2 optical density (OD) units in certain cases.

Reflective absorbance is particularly suitable for use with white microplates or any plate with a strong scatterer settled on the bottom, due to the strong scattering effect at the inner surface of the microplate wells. This scattering (and depolarizing) effect can be caused by the addition of a high dielectric constant material like titanium dioxide to the plastic from which the microplate is molded. Alternatively, scattering and depolarization can be caused by the presence of an optically active layer of small beads on the bottom of the well that have scattering properties (e.g., scintillation proximity assay (SPA) beads). The excitation light that is back-scattered from the well inner surface emerges from the microplate well highly depolarized. The use of crossed polarizers in the configuration shown in FIG. 15 causes back-reflected polarized light to be strongly attenuated by the second polarizer, enhancing the signal-to-background ratio. Highly polarized input light travels through the sample and is scattered and de-polarized when it hits the bottom surface of the microplate well. Back-scattered depolarized light that passed through the sample (and is absorbed or reflected by it) is preferentially passed through the crossed polarizers, whereas back-reflected polarized light from optical surfaces or the meniscus in the microplate well is highly attenuated because it retains a high polarization. In some applications, it may be possible to eliminate undesired contributions to a signal using two polarizers in alternative orientations, including generally parallel.

If the measurement conditions are optimized, reflective absorbance can be used in high throughput screening to detect and potentially correct for potential interferences from absorbing, scattering, compounds, targets, reagents, contaminants, etc. For example, reflective absorbance could be used to correct for color quenching in scintillation proximity assays or absorbing or luminescing compounds in intensity-based luminescence or chemiluminescence based assays.

Figure 16:
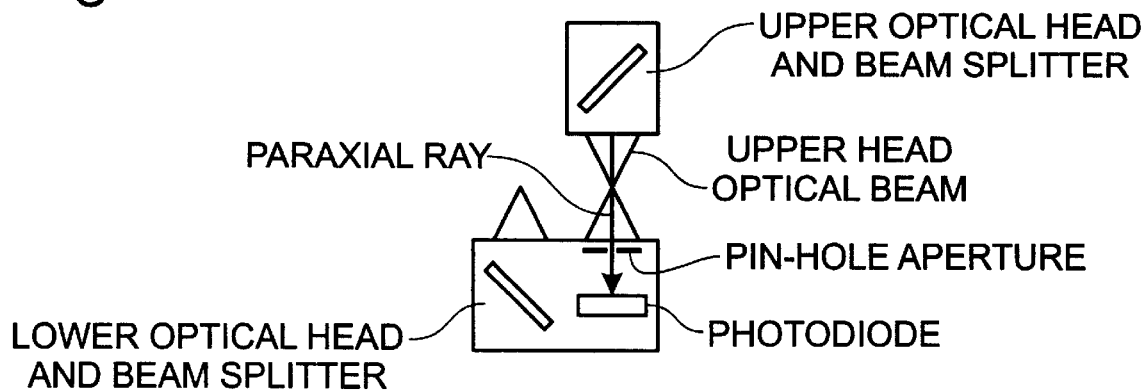
FIG. 16 is a schematic view of a system for measuring absorbance according to the invention.

FIG. 16 shows another system for measuring absorbance in a trans configuration according to the invention. In the disclosed embodiment described above, the detector takes the form of an upward-facing photodiode positioned directly below the optical axis of the upper head. A pin-hole aperture is disposed between the sample and the photodiode to limit the entry of light.

This system allows measurement of absorbance while luminescence or reflectance are measured by the optics in the upper head by the photomultiplier tube. The absorbance (or excitation) wavelength is selected using the excitation filter wheel. The reflectance or emission wavelength is selected using the emission filter wheel. A 50:50 beam splitter works well for absorbance/reflectance measurements, while a dichroic mirror may be more suitable from absorbance/luminescence measurements.

Measurement of absorbance in conjunction with other assays is useful in high-throughput screening. Abnormal absorbance measurements may indicate a quality-control problem, such as contamination or an air bubble. The absorbance data also could be used to detect or analyze false negatives or positives. It should be understood that the detector signal providing absorbance information may be processed to generate an actual absorbance value or may only be used to compute some quantity related to absorbance, such as a relative intensity of the signal.

An additional use for the design shown in FIG. 16 is to use the multi-mode measurement capabilities to determine location of reference fiducials on microplates, as described in U.S. patent application Ser. No. 09/156,318 and PCT patent application Ser. No. PCT/US99/08410, both of which are incorporated herein by reference. For example, transmission or reflection measurements can be used to detect a hole or other such optically identifiable feature on the surface of a microplate. The location of the fiducial can be determined by scanning the microplate under the detector while continuously measuring the transmission and searching for a maximum or minimum. The XYZ stage coordinates are recorded at each fiducial. This provides the location of fiducials in stage coordinates. Since the positions of the fiducials are known relative to other features on the plate, any feature on the plate can be accurately found by determining an appropriate offset from the known fiducial location.

6. Scattering Assays

Figure 17:
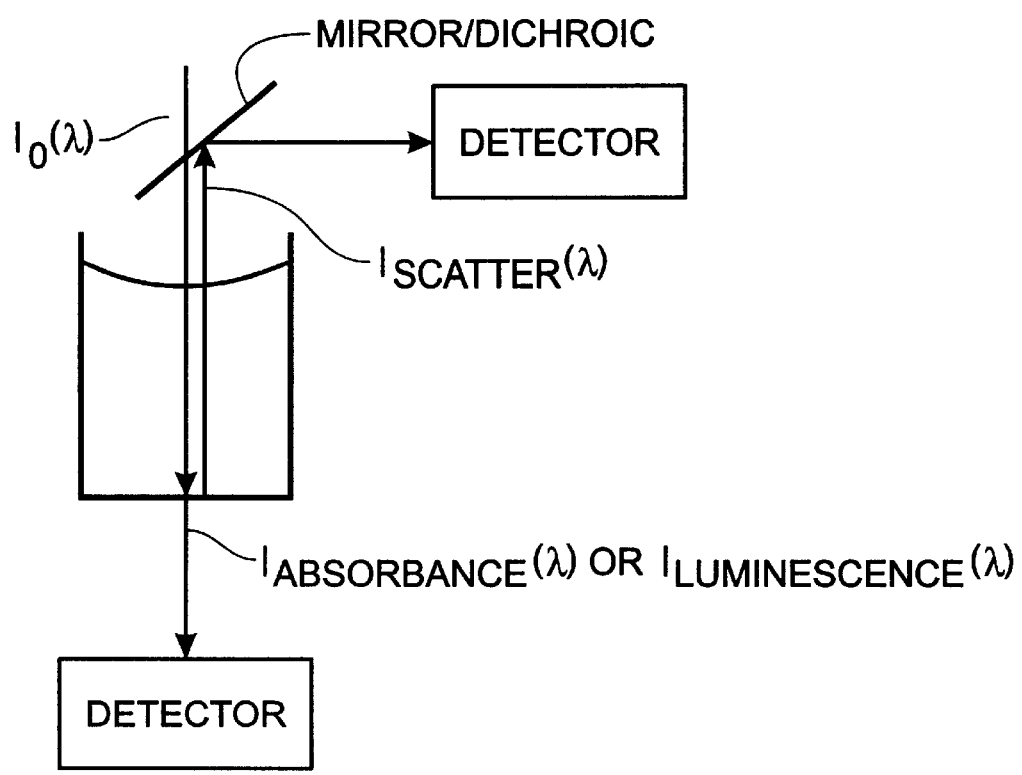
FIG. 17 is a schematic view of a system for measuring scattering according to the invention.

FIG. 17 schematically shows a scattering assay according to the invention in which scattered light is measured. Incident light $I_0$ is shone onto a sample. The sample includes a constituent that scatters the incident light. A component of the scattered light is received by a detector. The previously described technique of utilizing two polarizers also may be effective to reduce the effect of reflections on the scattering measurement. The best results for this type of scattering assay are obtained with a black or clear microplate that does not reflect or scatter significant amounts of the incident light.

A scattering assay according to the invention can be used alone or in conjunction with another spectroscopic assay. For example, the scattering assay can be conducted simultaneously with a luminescence assay to account for color quenching of the luminescence. In such a combined assay, the scattering is preferably monitored from the direction of the incident light as depicted in FIG. 17. Luminescence can be measured in either an epi- or trans- configuration as desired. This simultaneous measurement is facilitated by the wavelength (Stokes') shift of the luminescence relative to the incident (excitation) light, allowing separation of scattered and luminescence light.

It also is possible to conduct a combined scattering and absorbance assay. In a scattering/absorbance assay, the absorbance preferably is measured in the trans-direction, while the scattering preferably is measured in the epi-direction. It also is possible to conduct simultaneous scattering, luminescence and absorbance measurements by combining the scattering/absorbance, and scattering/luminescence assays. Moreover, it is also possible to conduct combined assays sequentially. In the case of sequential assays, it is possible to utilize the same detector for two or more types of measurements, such as scattering and luminescence.

Use of combined assays permits monitoring for various properties of the sample. Absorbance or scattering measurements outside a given range may indicate some problem with the sample, as described above. For example, an increase in scattering levels during a luminescence experiment can signal that a precipitate has formed in the sample, as might occur in a dilution series. Formation of a precipitate may decrease the luminescence signal. Without the scattering measurement, such a decrease might be falsely interpreted as a real decrease in the luminescence of the sample.

Although the invention has been disclosed in its preferred forms, the specific embodiments thereof as disclosed and illustrated herein are not to be considered in a limiting sense, because numerous variations are possible. Applicants regard the subject matter of their invention as including all novel and nonobvious combinations and subcombinations of the various elements, features, functions, and/or properties disclosed herein. No single feature, function, element or property of the disclosed embodiments is essential. For example, a reflective surface could be used in an absorbance assay in which light passes through one or more walls of the sample container, or single-pass illumination could be used in which light passes through an open side of the sample container. The following claims define certain combinations and subcombinations of features, functions, elements, and/or properties that are regarded as novel and nonobvious. Other combinations and subcombinations may be claimed through amendment of the present claims or presentation of new claims in this or a related application. Such claims, whether they are broader, narrower, equal, or different in scope than the original claims, also are regarded as included within the subject matter of applicants' invention.

We claim:

1. A method for measuring the temporal response properties of a luminescent sample, comprising:
    outputting a light beam from a light source, the light beam having a relatively constant intensity;
    modulating the light beam to create a modulated incident light, the modulated incident light having a maximum intensity that is substantially equal to the intensity of the light beam from the light source and a minimum intensity that is less than one-quarter of the maximum intensity;
    illuminating the sample with the modulated incident light, where the modulated incident light generates a modulated luminescence in the sample;
    measuring at least one of an amplitude and a phase of the modulated luminescence relative to the modulated incident light; and
    computing a temporal response characteristic of the sample based on the measured amplitude and/or phase.

2. The method of claim 1, wherein the step of measuring includes measuring both of an amplitude and a phase of the modulated luminescence relative to the modulated incident light.

3. The method of claim 1, wherein the step of computing includes calculating a temporal response characteristic of the sample based on the measured amplitude and phase.

4. The method of claim 1, wherein the temporal response characteristic is a luminescence lifetime or a rotational correlation time.

5. The method of claim 1, wherein the step of modulating is carried out at a fundamental frequency.

6. The method of claim 5, wherein the modulating generates a square wave.

7. The method of claim 6, wherein the modulated incident light has approximately zero minimum intensity.

8. The method of claim 5, wherein the step of measuring is carried out at the fundamental frequency and a harmonic thereof.

9. The method of claim 5, wherein the fundamental frequency is less than twenty kilohertz.

10. The method of claim 5, wherein the step of modulating is divided into a first part carried out at one fundamental frequency and a second part carried out at a second fundamental frequency.

11. The method of claim 1 further comprising the step of focusing the light beam into a focal plane during the step of modulating.

12. The method of claim 11, wherein the modulation is carried out with an optical modulator positioned proximal to the focal plane.

13. The method of claim 1, wherein the light source is a continuous arc lamp.

14. The method of claim 13, wherein the continuous arc lamp is a continuous high color temperature xenon arc lamp.

15. The method of claim 1, wherein the light source has a broad spectrum output.

16. The method of claim 1 further including the step of filtering the light beam to generate substantially monochromatic light.

17. An automated apparatus for conducting time-resolved spectroscopy, comprising:
   a light source;
   a system for directing light from the light source to a measurement region, the system including a light modulator configured to periodically modulate the intensity of light delivered to the measurement region;
   a stage configured to hold a plate containing a plurality of sample wells adapted to hold samples, the stage further being configured to place a selected one of the samples in the sample wells into the measurement region;
   a detector configured to receive luminescence light from a sample in the measurement region and generate a signal based on the amount of light received; and
   a signal processing system configured to track at least one of the phase and modulation of the signal relative to the phase and modulation of the modulated light delivered to the measurement region.

18. The apparatus of claim 17, wherein the signal processing system is configured to track both of the phase and modulation of the signal relative to the phase and modulation of the modulated light delivered to the measurement region.

19. The apparatus of claim 17, wherein the signal processing system includes a phase-locked loop coupled to the signal of the detector.

20. The apparatus of claim 19, wherein the light modulator has a fundamental frequency, and wherein the phase-locked loop is matched to the fundamental frequency.

21. The apparatus of claim 19, wherein the light modulator creates a square wave modulation of a fundamental frequency, and wherein the phase-locked loop is configured to track a harmonic of the fundamental frequency.

22. The apparatus of claim 17, wherein the light modulator is a chopper.

23. The apparatus of claim 22, wherein the system for directing light includes a mechanism focus light from the light source into a focal plane proximal to the chopper.

24. The apparatus of claim 23, wherein the focal plane is aligned with the chopper.

25. The apparatus of claim 22, wherein the chopper is selected from the group consisting of chopper wheels and tuning fork choppers.

26. The apparatus of claim 22, wherein the light modulator includes two choppers with different modulation frequencies.

27. The apparatus of claim 17, wherein the signal processing system includes a filter configured to receive the detector signal and extract a selected frequency component.

28. The apparatus of claim 27, wherein the signal processing system includes a second filter configured to receive the detector signal and extract a second selected frequency component.

29. The apparatus of claim 27, wherein the filter is a Bessel filter.

30. A method for performing a time-resolved spectroscopic assay, comprising:
   providing a light source with a broad spectrum output;
   extracting a substantially monochromatic component from the output of the light source;
   passing the monochromatic component through a chopper to create a periodically modulated incident light with a fundamental frequency;
   choosing a chopper duty cycle that produces a harmonic comparable to a selected time constant of the sample;
   generating luminescence in a sample by illuminating the sample with the modulated incident light; and
   detecting at least one of the phase and modulation of the luminescence relative to the modulated incident light.

31. The method of claim 30, wherein the step of detecting includes detecting both of the phase and modulation of the luminescence relative to the phase and modulation of the modulated incident light.

32. The method of claim 30 further comprising choosing a chopper modulation frequency that is comparable to a selected time constant of the sample.

33. The method of claim 32, wherein the selected time constant is greater than fifty microseconds.

34. The method of claim 30, wherein the light source is a continuous arc lamp.

35. The method of claim 34, wherein the continuous arc lamp is a continuous high color temperature xenon arc lamp.

36. The method of claim 30 further comprising the step of monitoring output intensity variations of the light source.

37. The method of claim 36 further comprising the step of correcting the measured amplitude of the modulated luminescence to compensate for intensity variations in the light source.

38. The method of claim 30, wherein the modulation of the incident light has the general form of a square wave.

39. The method of claim 30, wherein the step of detecting includes detecting the phase and/or modulation of the luminescence relative to the modulated incident light at a harmonic of the fundamental frequency.

40. The method of claim 30 further comprising the step of focusing the monochromatic component into a focal plane adjacent the chopper.

41. The assay of claim 30, wherein the light source has a substantially continuous output.

42. The method of claim 30, wherein the chopper is selected from the group consisting of chopper wheels and tuning fork choppers.

43. The method of claim 30 further comprising passing the monochromatic component through a second chopper to create a periodically modulated incident light with second fundamental frequency.

44. A method for performing a time-resolved spectroscopic assay, comprising:

provihding a light source with a broad spectrum output;

extracting a substantially monochromatic component from the output of the light source;

passing the monochromatic component through a chopper to create a periodically modulated incident light with a fundamental frequency;

generating luminescence in a sample by illuminating the sample with the modulated incident light;

monitoring output intensity variations of the light source;

correcting the measured amplitude of the modulated luminescence to compensate for intensity variations in the light source; and detecting at least one of the phase and modulation of the luminescence relative to the modulated incident light.

45. The method of claim 44, wherein the step of detecting includes detecting both of the phase and modulation of the luminescence relative to the phase and modulation of the modulated incident light.

46. The method of claim 44 further comprising choosing a chopper modulation frequency that is comparable to a selected time constant of the sample.

47. The method of claim 46, wherein the selected time constant is greater than fifty microseconds.

48. The method of claim 44, wherein the light source is a continuous arc lamp.

49. The method of claim 48, wherein the continuous arc lamp is a continuous high color temperature xenon arc lamp.

50. The method of claim 44, wherein the modulation of the incident light has the general form of a square wave.

51. The method of claim 44, wherein the step of detecting includes detecting the phase and/or modulation of the luminescence relative to the modulated incident light at a harmonic of the fundamental frequency.

52. The method of claim 44 further comprising the step of focusing the monochromatic component into a focal plane adjacent the chopper.

53. The assay of claim 44, wherein the light source has a substantially continuous output.

54. The method of claim 44, wherein the chopper is selected from the group consisting of chopper wheels and tuning fork choppers.

55. The method of claim 44 further comprising passing the monochromatic component through a second chopper to create a periodically modulated incident light with second fundamental frequency.

56. A method for performing a time-resolved spectroscopic assay, comprising:

providing a light source with a broad spectrum output;

extracting a substantially monochromatic component from the output of the light source;

passing the monochromatic component through a chopper to create a periodically modulated incident light with a fundamental frequency, wherein the modulation of the incident light has the general form of the square wave;

generating luminescence in a sample by illuminating the sample with the modulated incident light; and detecting at least one of the phase and modulation of the luminescence relative to the modulated incident light.

57. The method of claim 56, wherein the step of detecting includes detecting both of the phase and modulation of the luminescence relative to the phase and modulation of the modulated incident light.

58. The method of claim 56 further comprising choosing a chopper modulation frequency that is comparable to a selected time constant of the sample.

59. The method of claim 58, wherein the selected time constant is greater than fifty microseconds.

60. The method of claim 56, wherein the light source is a continuous arc lamp.

61. The method of claim 60, wherein the continuous arc lamp is a continuous high color temperature xenon arc lamp.

62. The method of claim 56, wherein the step of detecting includes detecting the phase and/or modulation of the luminescence relative to the modulated incident light at a harmonic of the fundamental frequency.

63. The method of claim 56 further comprising the step of focusing the monochromatic component into a focal plane adjacent the chopper.

64. The assay of claim 56, wherein the light source has a substantially continuous output.

65. The method of claim 56, wherein the chopper is selected from the group consisting of chopper wheels and tuning fork choppers.

66. The method of claim 56 further comprising passing the monochromatic component through a second chopper to create a periodically modulated incident light with second fundamental frequency.

67. A method for performing a time-resolved spectroscopic assay, comprising:

providing a light source with a broad spectrum output;

extracting a substantially monochromatic component from the output of the light source;

passing the monochromatic component through a chopper to create a periodically modulated incident light with a fundamental frequency;

generating luminescence in a sample by illuminating the sample with the modulated incident light; and detecting at least one of the phase and modulation of the luminescence relative to the modulated incident light, wherein the step of detecting includes detecting the phase and/or modulation of the luminescence relative to the modulated incident light at a harmonic of the fundamental frequency.

68. The method of claim 67, wherein the step of detecting includes detecting both of the phase and modulation of the luminescence relative to the phase and modulation of the modulated incident light.

69. The method of claim 67 further comprising choosing a chopper modulation frequency that is comparable to a selected time constant of the sample.

70. The method of claim 69, wherein the selected time constant is greater than fifty microseconds.

71. The method of claim 67, wherein the light source is a continuous arc lamp.

72. The method of claim 71, wherein the continuous arc lamp is a continuous high color temperature xenon arc lamp.

73. The method of claim 67 further comprising the step of focusing the monochromatic component into a focal plane adjacent the chopper.

74. The assay of claim 67, wherein the light source has a substantially continuous output.

75. The method of claim 67, wherein the chopper is selected from the group consisting of chopper wheels and tuning fork choppers.

76. The method of claim 67 further comprising passing the monochromatic component through a second chopper to create a periodically modulated incident light with second fundamental frequency.

77. A method for performing a time-resolved spectroscopic assay, comprising:
   providing a light source with a broad spectrum output;
   extracting a substantially monochromatic component from the output of the light source;
   focusing the monochromatic component into a focal plane adjacent a chopper;
   passing the monochromatic component through a chopper to create a periodically modulated incident light with a fundamental frequency;
   generating luminescence in a sample by illuminating the sample with the modulated incident light; and
   detecting at least one of the phase and modulation of the luminescence relative to the modulated incident light.

78. The method of claim 77, wherein the step of detecting includes detecting both of the phase and modulation of the luminescence relative to the phase and modulation of the modulated incident light.

79. The method of claim 77 further comprising choosing a chopper modulation frequency that is comparable to a selected time constant of the sample.

80. The method of claim 79, wherein the selected time constant is greater than fifty microseconds.

81. The method of claim 77, wherein the light source is a continuous arc lamp.

82. The method of claim 81, wherein the continuous arc lamp is a continuous high color temperature xenon arc lamp.

83. The assay of claim 77, wherein the light source has a substantially continuous output.

84. The method of claim 77, wherein the chopper is selected from the group consisting of chopper wheels and tuning fork choppers.

85. The method of claim 77 further comprising passing the monochromatic component through a second chopper to create a periodically modulated incident light with second fundamental frequency.

86. A method for performing a time-resolved spectroscopic assay, comprising:
   providing a light source with a broad spectrum output;
   extracting a substantially monochromatic component from the output of the light source;
   passing the monochromatic component through a chopper to create a periodically modulated incident light with a fundamental frequency;
   generating luminescence in a sample by illuminating the sample with the modulated incident light; and
   detecting at least one of the phase and modulation of the luminescence relative to the modulated incident light.

87. The method of claim 86, wherein the step of detecting includes detecting both of the phase and modulation of the luminescence relative to the phase and modulation of the modulated incident light.

88. The method of claim 86 further comprising choosing a chopper modulation frequency that is comparable to a selected time constant of the sample.

89. The method of claim 86, wherein the selected time constant is greater than fifty microseconds.

90. The method of claim 86, wherein the light source is a continuous arc lamp.

91. The method of claim 90, wherein the continuous arc lamp is a continuous high color temperature xenon arc lamp.

92. The method of claim 86, wherein the chopper is selected from the group consisting of chopper wheels and tuning fork choppers.

93. The method of claim 86 further comprising passing the monochromatic component through a second chopper to create a periodically modulated incident light with second fundamental frequency.

94. A method for performing a time-resolved spectroscopic assay, comprising:
   providing a light source with a broad spectrum output;
   extracting a substantially monochromatic component from the output of the light source;
   passing the monochromatic component through a chopper to create a periodically modulated incident light with a fundamental frequency, wherein the chopper is selected from the group consisting of chopper wheels and tuning fork choppers;
   generating luminescence in a sample by illuminating the sample with the modulated incident light; and
   detecting at least one of the phase and modulation of the luminescence relative to the modulated incident light.

95. The method of claim 94, wherein the step of detecting includes detecting both of the phase and modulation of the luminescence relative to the phase and modulation of the modulated incident light.

96. The method of claim 94 further comprising choosing a chopper modulation frequency that is comparable to a selected time constant of the sample.

97. The method of claim 96, wherein the selected time constant is greater than fifty microseconds.

98. The method of claim 94, wherein the light source is a continuous arc lamp.

99. The method of claim 98, wherein the continuous arc lamp is a continuous high color temperature xenon arc lamp.

100. The method of claim 94 further comprising passing the monochromatic component through a second chopper to create a periodically modulated incident light with second fundamental frequency.

101. A method for performing a time-resolved spectroscopic assay, comprising:
   providing a light source with a broad spectrum output;
   extracting a substantially monochromatic component from the output of the light source;
   passing the monochromatic component through a chopper to create a periodically modulated incident light with a fundamental frequency;
   generating luminescence in a sample by illuminating the sample with the modulated incident light; and
   detecting at least one of the phase and modulation of the luminescence relative to the modulated incident light.

102. The method of claim 101, wherein the step of detecting includes detecting both of the phase and modulation of the luminescence relative to the phase and modulation of the modulated incident light.

103. The method of claim 101 further comprising choosing a chopper modulation frequency that is comparable to a selected time constant of the sample.

104. The method of claim 103, wherein the selected time constant is greater than fifty microseconds.

105. The method of claim 101, wherein the light source is a continuous arc lamp.

106. The method of claim 98, wherein the continuous arc lamp is a continuous high color temperature xenon arc lamp.

* * * * *

UNITED STATES PATENT AND TRADEMARK OFFICE
CERTIFICATE OF CORRECTION

PATENT NO. : 6,483,582 B2
DATED : November 19, 2002
INVENTOR(S) : Douglas N. Modlin, Todd E. French and John C. Owicki It is certified that error appears in the above-identified patent and that said Letters Patent is hereby corrected as shown below:

Column 28,
Line 23, delete "for" and insert -- of -- therefor.
Line 66, delete "assay" and insert -- method -- therefor.

Column 29,
Line 6, after "with" insert -- a --.
Line 8, delete "for" and insert -- of -- therefor.
Line 47, delete "assay" and insert -- method -- therefor.
Line 54, after "with" insert -- a --.
Line 56, delete "for" and insert -- of -- therefor.
Line 65, after "of" delete "the" and insert -- a -- therefor.

Column 30,
Line 22, delete "assay" and insert -- method -- therefor.
Line 28, after "with" insert -- a --.
Line 31, delete "for" and insert -- of -- therefor.
Line 63, delete "assay" and insert -- method -- therefor.

Column 31,
Line 3, after "with" insert -- a --.
Lines 5 and 42, delete "for" and insert -- of -- therefor.
Line 13, delete "a" and insert -- the -- therefor.
Line 35, delete "assay" and insert -- method -- therefor.
Line 40, after "with" insert -- a --.
Line 44, after "with a" insert -- substantially continuous, --.

UNITED STATES PATENT AND TRADEMARK OFFICE
CERTIFICATE OF CORRECTION

PATENT NO. : 6,483,582 B2
DATED : November 19, 2002
INVENTOR(S) : Douglas N. Modlin, Todd E. French and John C. Owicki It is certified that error appears in the above-identified patent and that said Letters Patent is hereby corrected as shown below:

<u>Column 32,</u>
Line 6, after "with" insert -- a --.
Line 8, delete "for" and insert -- of -- therefor.
Line 36, after "with" insert -- a --.
Line 40, delete "for" and insert -- of -- therefor.
After line 48 and before line 49, insert the following new paragraph:
-- passing the monochromatic component through a second chopper to create a periodically modulated incident light with a second fundamental frequency; --.

Signed and Sealed this

First Day of July, 2003

JAMES E. ROGAN
*Director of the United States Patent and Trademark Office*